(12) United States Patent
Shortt et al.

(10) Patent No.: US 6,821,119 B2
(45) Date of Patent: *Nov. 23, 2004

(54) DUAL MOTOR ORAL HYGIENE DEVICE

(75) Inventors: Robert A. Shortt, Laguna Niguel, CA (US); Kenneth A. Hair, Fort Collins, CO (US); Kurt M. Taylor, Fort Collins, CO (US); Daniel E. Julian, Athens, IL (US); Edmund D. D'Silva, Loveland, CO (US)

(73) Assignee: Water Pik, Inc., Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/194,201

(22) Filed: Jul. 12, 2002

(65) Prior Publication Data

US 2003/0031979 A1 Feb. 13, 2003

Related U.S. Application Data

(60) Provisional application No. 60/347,577, filed on Jan. 11, 2002, and provisional application No. 60/305,413, filed on Jul. 12, 2001.

(51) Int. Cl.[7] .............................................. A61C 3/03
(52) U.S. Cl. ...................................................... 433/118
(58) Field of Search ................................ 433/118, 119, 433/125, 117, 114, 166, 124, 131, 133; 132/322, 309; 15/167.1

(56) References Cited

U.S. PATENT DOCUMENTS

| | | |
|---|---|---|
| 1,313,490 A | 8/1919 | Larson |
| 1,355,037 A | 10/1920 | Dziuk |
| 1,424,879 A | 8/1922 | Carlstedt |

(List continued on next page.)

FOREIGN PATENT DOCUMENTS

| | | |
|---|---|---|
| CH | 435553 | 10/1967 |
| CH | 609238 | 2/1979 |
| DE | 243224 | 4/1910 |

(List continued on next page.)

OTHER PUBLICATIONS

Sonex International: Brushing with the Ultima—The World's Only Dual–Frequency Ultrasonic Toothbrush, Jul. 28, 1999, published at Sonipic.com.

Teledyne Water Pik "Plaque Control 3000" plaque removal instrument (Jul. 1991).

American Dentronics Incorporated "Soniplak" sonic plaque removal system (May 1993).

Design of a Toothbrush, p. 361, Danish Official Design Gazette, published May 16, 1997.

Teledyne Water Pik "Sensonic" Toothbrush, sales brochure (at least as early as Sep. 1994).

*Primary Examiner*—Kevin Shaver
*Assistant Examiner*—Melba Bumgarner
(74) *Attorney, Agent, or Firm*—Dorsey & Whitney LLP

(57) ABSTRACT

An oral hygiene device (2) is disclosed having at least two motors (30, 36) to simultaneously vibrate and impart motion upon the head portion of the oral hygiene device (2), most beneficially at the tip (12). A first motor (30) is positioned in the handle housing (3) of the device (2) to impart a first frequency of movement to the tip (12). A second motor (36) is located in a head portion, generally in a shaft (8) of or an oral hygiene attachment to the device (2), to impart at least a second frequency of movement onto the tip (12). When both the first and second motors (30, 36) are activated, the resulting movement of the tip (12) of the device (2) may include complex, substantially random movements, depending in part on the frequencies at which the motors (30, 36) are operating.

49 Claims, 21 Drawing Sheets

U.S. PATENT DOCUMENTS

| | | |
|---|---|---|
| 1,517,320 A | 12/1924 | Stoddart |
| 1,696,835 A | 12/1928 | Burnett |
| 1,703,642 A | 2/1929 | Sticht |
| 1,796,641 A | 3/1931 | Zimmerman et al. |
| 1,832,519 A | 11/1931 | Wheat et al. |
| 2,016,597 A | 10/1935 | Drake |
| 2,044,863 A | 6/1936 | Sticht |
| 2,158,738 A | 5/1939 | Baker et al. |
| 2,206,726 A | 7/1940 | Lasater |
| 2,246,523 A | 6/1941 | Kulik |
| 2,278,365 A | 3/1942 | Daniels |
| 2,282,700 A | 5/1942 | Bobbroff |
| 2,598,275 A | 5/1952 | Lakin ............................ 74/36 |
| 2,709,227 A | 5/1955 | Foley et al. |
| 2,728,928 A | 1/1956 | Beeren ......................... 15/29 |
| 2,734,139 A | 2/1956 | Murphy ....................... 310/29 |
| 2,806,235 A | 9/1957 | Carstairs et al. ............... 15/22 |
| 2,875,458 A | 3/1959 | Tsuda ........................... 15/22 |
| 2,917,758 A | 12/1959 | Held et al. .................... 15/22 |
| 2,931,371 A | 4/1960 | Petitta ......................... 132/89 |
| 2,977,614 A | 4/1961 | Demanuele .................. 15/22 |
| 3,104,405 A | 9/1963 | Perrinjaquet ................. 15/22 |
| 3,106,216 A | 10/1963 | Kirby .......................... 132/92 |
| D197,048 S | 12/1963 | Troy ............................. D9/2 |
| D197,208 S | 12/1963 | Cassidy et al. ................. D9/2 |
| 3,143,697 A | 8/1964 | Springer ....................... 320/2 |
| 3,145,404 A | 8/1964 | Fiedler ......................... 15/23 |
| D199,560 S | 11/1964 | Thompson ..................... D9/2 |
| D199,893 S | 12/1964 | Bond et al. .................... D9/2 |
| 3,159,859 A | 12/1964 | Rasmussen .................... 15/22 |
| 3,181,189 A | 5/1965 | Leyden ......................... 15/22 |
| 3,183,538 A | 5/1965 | Hubner ......................... 15/22 |
| D202,873 S | 11/1965 | Husted .......................... D9/2 |
| D204,127 S | 3/1966 | Syvertson ...................... D9/2 |
| 3,270,416 A | 9/1966 | Massa ........................... 32/22 |
| 3,316,576 A | 5/1967 | Urbrush ........................ 15/22 |
| 3,335,443 A | 8/1967 | Parisi et al. .................... 15/22 |
| 3,346,748 A | 10/1967 | McNair ........................ 310/16 |
| 3,358,309 A | 12/1967 | Richardson .................... 15/22 |
| 3,371,260 A | 2/1968 | Jackson et al. ................. 320/2 |
| 3,375,820 A | 4/1968 | Kuris et al. ................... 128/62 |
| D212,208 S | 9/1968 | Rogers ......................... D4/16 |
| 3,418,552 A | 12/1968 | Holmes ........................ 320/2 |
| 3,430,279 A | 3/1969 | Hintze .......................... 15/23 |
| 3,463,994 A | 8/1969 | Spohr ........................... 320/2 |
| 3,466,689 A | 9/1969 | Aurelio et al. ................. 15/22 |
| 3,472,045 A | 10/1969 | Nelsen et al. .................. 64/4 |
| 3,472,247 A | 10/1969 | Borsum et al. ............... 132/91 |
| 3,474,799 A | 10/1969 | Cappello ..................... 132/91 |
| 3,535,726 A | 10/1970 | Sawyer ......................... 15/22 |
| 3,538,359 A | 11/1970 | Barowski ..................... 310/29 |
| 3,552,022 A | 1/1971 | Axelsson ....................... 32/58 |
| 3,559,292 A | 2/1971 | Weissman ..................... 33/163 |
| 3,563,233 A | 2/1971 | Bodine ......................... 128/36 |
| 3,588,936 A | 6/1971 | Duve ............................ 15/22 |
| D221,823 S | 9/1971 | Cook ........................... D4/15 |
| 3,642,344 A | 2/1972 | Corker ......................... 350/6 |
| 3,651,576 A | 3/1972 | Massa ........................ 32/40 R |
| 3,660,902 A | 5/1972 | Axelsson ....................... 32/58 |
| 3,672,378 A | 6/1972 | Silverman .................... 132/93 |
| 3,676,218 A | 7/1972 | Sawyer ......................... 134/1 |
| 3,759,274 A | 9/1973 | Warner ...................... 132/92 R |
| 3,760,799 A | 9/1973 | Crowson .................... 128/24 A |
| 3,809,977 A | 5/1974 | Balamuth et al. ......... 318/221 R |
| 3,831,611 A | 8/1974 | Hendricks ................. 132/92 R |
| 3,840,932 A | 10/1974 | Balamuth et al. .......... 15/167 R |
| 3,882,364 A | 5/1975 | Wright et al. ........... 318/221 R |
| 3,902,510 A | 9/1975 | Roth ......................... 132/92 A |
| 3,903,601 A | 9/1975 | Anderson et al. ........... 32/14 D |
| 3,967,617 A | 7/1976 | Krolik ......................... 128/36 |
| 3,978,852 A | 9/1976 | Annoni ....................... 128/62 A |
| 3,980,906 A | 9/1976 | Kuris et al. .................. 310/8.1 |
| 4,004,344 A | 1/1977 | Gold et al. ..................... 32/27 |
| 4,005,722 A | 2/1977 | Bragg ....................... 132/92 R |
| 4,008,728 A | 2/1977 | Sanchez .................... 132/92 R |
| 4,019,522 A | 4/1977 | Elbreder ...................... 132/90 |
| 4,048,723 A | 9/1977 | Thorup ...................... 32/40 R |
| 4,064,883 A | 12/1977 | Oldham ...................... 132/93 |
| 4,133,339 A | 1/1979 | Naslund ...................... 132/89 |
| 4,177,434 A | 12/1979 | Ida .............................. 331/27 |
| D254,162 S | 2/1980 | Barker ......................... D4/15 |
| 4,192,035 A | 3/1980 | Kuris ......................... 15/22 R |
| 4,203,431 A | 5/1980 | Abura et al. ................. 128/39 |
| 4,205,664 A | 6/1980 | Baccialon ................. 128/62 A |
| 4,219,619 A | 8/1980 | Zarow ........................ 433/118 |
| 4,235,253 A | 11/1980 | Moore ...................... 132/92 R |
| RE30,536 E | 3/1981 | Perdreaux, Jr. ............... 433/86 |
| 4,255,693 A | 3/1981 | Keidl ......................... 318/685 |
| 4,271,382 A | 6/1981 | Maeda et al. ............... 318/318 |
| 4,271,384 A | 6/1981 | Beling et al. ............... 318/685 |
| 4,275,363 A | 6/1981 | Mishiro et al. ................ 331/4 |
| 4,289,486 A | 9/1981 | Sargeant ..................... 433/118 |
| 4,307,740 A | 12/1981 | Florindez et al. ......... 132/92 R |
| 4,319,377 A | 3/1982 | Tarrson et al. ................ 15/111 |
| 4,319,595 A | 3/1982 | Ulrich ...................... 132/92 R |
| 4,326,547 A | 4/1982 | Verplank ..................... 132/89 |
| 4,326,548 A | 4/1982 | Wagner ....................... 132/90 |
| 4,331,422 A | 5/1982 | Heyman ..................... 433/125 |
| 4,333,197 A | 6/1982 | Kuris ......................... 15/22 R |
| D265,515 S | 7/1982 | Levine ........................ D24/99 |
| 4,338,957 A | 7/1982 | Meibauer ................... 132/91 |
| 4,347,839 A | 9/1982 | Youngclaus, Jr. ......... 128/62 A |
| 4,353,141 A | 10/1982 | Teague, Jr. et al. ......... 15/22 R |
| 4,381,478 A | 4/1983 | Saijo et al. ................. 318/135 |
| 4,395,665 A | 7/1983 | Buchas ....................... 318/114 |
| 4,397,327 A | 8/1983 | Hadary ....................... 132/89 |
| D272,565 S | 2/1984 | Levine ........................ D24/99 |
| D272,680 S | 2/1984 | Stocchi ........................ D4/25 |
| 4,429,997 A | 2/1984 | Matthews ................... 356/350 |
| 4,432,729 A | 2/1984 | Fattaleh ...................... 433/118 |
| 4,434,806 A | 3/1984 | Givens ....................... 132/91 |
| 4,442,830 A | 4/1984 | Markau ...................... 128/66 |
| 4,458,702 A | 7/1984 | Grollimund ................. 132/92 |
| 4,505,678 A | 3/1985 | Andersson .................. 433/143 |
| 4,522,355 A | 6/1985 | Moran ........................ 244/3.2 |
| 4,562,413 A | 12/1985 | Mishiro et al. .......... 331/116 R |
| 4,564,794 A | 1/1986 | Kilen et al. ................. 318/314 |
| 4,576,190 A | 3/1986 | Youssef ...................... 132/89 |
| 4,577,649 A | 3/1986 | Shimenkov ................. 132/93 |
| D283,374 S | 4/1986 | Cheuk-Yiu .................. D4/101 |
| 4,585,415 A | 4/1986 | Hommann .................. 433/80 |
| 4,603,448 A * | 8/1986 | Middleton et al. ......... 15/22.1 |
| 4,605,025 A | 8/1986 | McSpadden .............. 132/92 R |
| 4,608,019 A | 8/1986 | Kumabe et al. ............. 433/118 |
| 4,617,718 A | 10/1986 | Andersson .................... 29/558 |
| 4,634,376 A | 1/1987 | Mossle et al. ................ 433/29 |
| 4,644,937 A | 2/1987 | Hommann .................. 128/66 |
| 4,655,198 A | 4/1987 | Hommann .................. 128/66 |
| 4,698,869 A | 10/1987 | Mierau et al. ............. 15/22 R |
| D294,885 S | 3/1988 | Mollenhoff ................ D4/101 |
| 4,766,630 A | 8/1988 | Hegemann ................ 15/22 R |
| 4,787,847 A | 11/1988 | Martin et al. ............... 433/119 |
| 4,791,940 A | 12/1988 | Hirschfeld et al. ......... 128/776 |
| 4,811,445 A | 3/1989 | Lagieski et al. ......... 15/104.94 |
| 4,820,153 A | 4/1989 | Romhild et al. ............ 433/118 |
| 4,820,154 A | 4/1989 | Romhild et al. ............ 433/128 |
| 4,827,550 A | 5/1989 | Graham et al. ............ 15/22 R |
| 4,832,063 A | 5/1989 | Smole ........................ 132/329 |
| 4,845,795 A | 7/1989 | Crawford et al. .......... 15/22 R |
| 4,856,133 A | 8/1989 | Sanchez ..................... 15/29 |
| D303,876 S | 10/1989 | Clemens et al. ............ D4/101 |

| | | | | | |
|---|---|---|---|---|---|
| 4,871,396 A | 10/1989 | Tsujita et al. .............. 106/286.8 | 5,358,328 A | 10/1994 | Inoue et al. ................... 366/65 |
| 4,873,496 A | 10/1989 | Ohgihara et al. ............... 331/96 | 5,359,747 A | 11/1994 | Amakasu ..................... 15/22.1 |
| 4,880,382 A | 11/1989 | Moret et al. ................. 433/118 | D353,490 S | 12/1994 | Hartwein ...................... D4/108 |
| 4,887,052 A | 12/1989 | Murakami et al. ............. 331/96 | 5,369,831 A | 12/1994 | Bock ............................ 15/22.1 |
| 4,913,133 A | 4/1990 | Tichy ....................... 128/62 A | D354,168 S | 1/1995 | Hartwein ...................... D4/108 |
| 4,922,936 A | 5/1990 | Buzzi et al. .................. 132/321 | 5,378,153 A | 1/1995 | Giuliani et al. .............. 433/216 |
| 4,974,278 A | 12/1990 | Hommann .................. 15/22 R | 5,383,242 A | 1/1995 | Bigler et al. ................. 15/22.1 |
| 4,989,287 A | 2/1991 | Scherer ....................... 15/22.1 | 5,393,229 A | 2/1995 | Ram ........................... 433/118 |
| 4,991,249 A | 2/1991 | Suroff .......................... 15/22.2 | 5,404,608 A | 4/1995 | Hommann ................... 15/22.1 |
| 4,995,403 A | 2/1991 | Beckman et al. ............. 128/776 | 5,406,664 A | 4/1995 | Hukuba ........................ 15/22.1 |
| 5,000,684 A | 3/1991 | Odrich ......................... 433/125 | 5,406,965 A | 4/1995 | Levine ......................... 132/323 |
| 5,002,487 A | 3/1991 | Tichy ........................... 433/122 | D358,486 S | 5/1995 | Loew ........................... D4/104 |
| 5,007,127 A | 4/1991 | Paolo ............................. 15/29 | D358,713 S | 5/1995 | Perry ........................... D4/104 |
| 5,016,660 A | 5/1991 | Boggs ........................ 132/322 | D358,801 S | 5/1995 | Vos ............................ D13/108 |
| 5,020,179 A | 6/1991 | Scherer ....................... 15/22.1 | 5,411,041 A | 5/1995 | Ritter ........................... 132/322 |
| D319,363 S | 8/1991 | Uemura et al. .............. D6/534 | 5,412,827 A | 5/1995 | Muller et al. ................. 15/22.1 |
| 5,050,625 A | 9/1991 | Siekmann .................. 132/323 | 5,416,942 A | 5/1995 | Baldacci et al. .............. 15/22.1 |
| D321,285 S | 11/1991 | Hirabayashi ................. D4/101 | 5,419,346 A | 5/1995 | Tipp ............................ 132/329 |
| 5,067,223 A | 11/1991 | Bruno ......................... 29/426.5 | 5,419,703 A | 5/1995 | Warrin et al. ................ 433/216 |
| D321,986 S | 12/1991 | Snyder et al. ................ D4/101 | 5,421,726 A | 6/1995 | Okada ......................... 433/216 |
| 5,068,939 A | 12/1991 | Holland ....................... 15/22.1 | D363,605 S | 10/1995 | Kou et al. .................... D4/101 |
| 5,069,621 A | 12/1991 | Paradis ........................ 433/147 | 5,459,898 A | 10/1995 | Bacolot ......................... 15/106 |
| 5,071,348 A | 12/1991 | Woog .......................... 433/118 | 5,467,494 A | 11/1995 | Muller et al. ................. 15/22.1 |
| 5,072,477 A | 12/1991 | Pai .............................. 15/22.1 | 5,467,495 A | 11/1995 | Boland et al. ................... 15/28 |
| 5,072,482 A | 12/1991 | Bojar et al. .................... 15/180 | 5,482,466 A | 1/1996 | Haynes ........................ 132/323 |
| 5,077,855 A | 1/1992 | Ambasz ....................... 15/22.1 | 5,484,281 A | 1/1996 | Renow et al. ................. 433/80 |
| 5,088,145 A | 2/1992 | Whitefield .................. 15/22.1 | 5,496,256 A | 3/1996 | Bock et al. ..................... 601/2 |
| 5,094,256 A | 3/1992 | Barth ........................... 132/322 | 5,499,420 A | 3/1996 | Boland ......................... 15/22.1 |
| 5,095,470 A | 3/1992 | Oka et al. ..................... 369/13 | 5,504,958 A | 4/1996 | Herzog ......................... 15/22.1 |
| 5,100,321 A | 3/1992 | Coss et al. ................... 433/118 | 5,511,270 A | 4/1996 | Eliachar et al. ............... 15/22.1 |
| 5,120,225 A | 6/1992 | Amit ........................... 433/216 | 5,511,275 A | 4/1996 | Volpenhein et al. ......... 15/167.1 |
| 5,123,841 A | 6/1992 | Millner ........................ 433/125 | D370,125 S | 5/1996 | Craft et al. .................... D4/101 |
| 5,125,837 A | 6/1992 | Warrin et al. ................. 433/98 | D370,347 S | 6/1996 | Heinzelman et al. ......... D4/104 |
| 5,133,661 A | 7/1992 | Euvrard ....................... 433/120 | 5,529,494 A | 6/1996 | Vlacancich .................. 433/105 |
| 5,138,733 A | 8/1992 | Bock ............................ 15/22.1 | 5,546,624 A | 8/1996 | Bock ............................ 15/22.1 |
| 5,145,369 A | 9/1992 | Lustig et al. ................ 433/118 | D375,841 S | 11/1996 | Serbinski ..................... D4/108 |
| 5,150,492 A | 9/1992 | Suroff ......................... 15/22.1 | 5,573,020 A | 11/1996 | Robinson .................... 132/322 |
| 5,165,131 A | 11/1992 | Staar ............................ 15/22.1 | 5,577,285 A | 11/1996 | Drossler ....................... 15/22.1 |
| 5,169,313 A | 12/1992 | Kline ........................... 433/143 | 5,579,786 A | 12/1996 | Wolk et al. ................... 132/322 |
| 5,170,809 A | 12/1992 | Imai et al. ................... 132/322 | 5,606,984 A | 3/1997 | Gao ............................. 132/325 |
| 5,174,314 A | 12/1992 | Charatan ..................... 132/328 | 5,613,258 A | 3/1997 | Hilfinger et al. .............. 15/22.1 |
| 5,177,826 A | 1/1993 | Vrignaud et al. ............. 15/22.1 | 5,613,259 A | 3/1997 | Craft et al. .................... 15/22.1 |
| 5,180,363 A | 1/1993 | Idemoto et al. ................ 202/32 | 5,617,601 A | 4/1997 | McDougall ................... 15/22.1 |
| 5,183,063 A | 2/1993 | Ringle et al. ................. 132/321 | 5,618,275 A | 4/1997 | Bock ........................... 604/290 |
| 5,189,751 A | 3/1993 | Giuliani et al. .............. 15/22.1 | 5,619,766 A | 4/1997 | Zhadanov et al. ............. 15/29 |
| 5,198,732 A | 3/1993 | Morimoto .................... 318/116 | 5,625,916 A | 5/1997 | McDougall ..................... 15/28 |
| 5,201,092 A | 4/1993 | Colson ....................... 15/167.1 | 5,651,157 A | 7/1997 | Hahn ........................... 15/22.1 |
| 5,213,434 A | 5/1993 | Hahn ........................... 403/59 | D382,407 S | 8/1997 | Craft et al. .................... D4/101 |
| 5,214,819 A | 6/1993 | Kirchner ..................... 15/22.1 | 5,652,990 A | 8/1997 | Driesen et al. ................. 15/28 |
| 5,224,500 A | 7/1993 | Stella .......................... 132/322 | 5,678,274 A | 10/1997 | Liu ........................... 15/167.1 |
| 5,226,206 A | 7/1993 | Davidovitz et al. .......... 15/22.1 | 5,697,117 A | 12/1997 | Craft ........................... 15/22.1 |
| 5,236,358 A | 8/1993 | Sieffert ....................... 433/119 | 5,700,146 A | 12/1997 | Kucar ........................... 433/82 |
| 5,247,716 A | 9/1993 | Bock ............................ 15/22.1 | 5,709,233 A | 1/1998 | Boland et al. .............. 132/322 |
| 5,253,382 A | 10/1993 | Beny ........................... 15/22.1 | 5,718,667 A | 2/1998 | Sugimoto et al. ............ 601/139 |
| 5,261,430 A | 11/1993 | Mochel ....................... 132/322 | 5,732,433 A | 3/1998 | Göcking et al. ................. 15/28 |
| 5,263,218 A | 11/1993 | Giuliani et al. .............. 15/22.1 | 5,738,575 A | 4/1998 | Bock ........................... 433/216 |
| D341,943 S | 12/1993 | Si-Hoe ......................... D4/108 | 5,742,972 A | 4/1998 | Bredall et al. ............... 15/167.1 |
| 5,289,604 A | 3/1994 | Kressner ..................... 15/22.1 | 5,784,742 A * | 7/1998 | Giuliani et al. .............. 15/22.1 |
| 5,293,886 A | 3/1994 | Czapor ........................ 132/329 | 5,784,743 A | 7/1998 | Shek ............................ 15/22.1 |
| 5,294,896 A | 3/1994 | Kjellander et al. ........... 331/158 | 5,787,908 A | 8/1998 | Robinson .................... 132/322 |
| 5,305,492 A | 4/1994 | Giuliani et al. ............. 15/176.1 | 5,794,295 A | 8/1998 | Shen ............................ 15/22.1 |
| 5,309,590 A | 5/1994 | Giuliani et al. .............. 15/22.1 | 5,815,872 A | 10/1998 | Meginniss, III et al. ...... 15/22.1 |
| 5,309,591 A | 5/1994 | Hägele et al. ................ 15/22.1 | 5,827,064 A | 10/1998 | Bock ........................... 433/216 |
| 5,311,632 A | 5/1994 | Center ......................... 15/22.1 | D400,713 S | 11/1998 | Solanki ........................ D4/104 |
| 5,311,633 A | 5/1994 | Herzog et al. .................. 15/28 | 5,836,030 A | 11/1998 | Hazeu et al. ................. 15/22.1 |
| 5,323,796 A | 6/1994 | Urso ........................... 132/322 | 5,842,244 A | 12/1998 | Hilfinger et al. .............. 15/22.1 |
| 5,337,435 A | 8/1994 | Krasner et al. ................ 15/23 | 5,850,655 A | 12/1998 | Göcking et al. ................. 15/28 |
| 5,341,534 A | 8/1994 | Serbinski et al. ............ 15/22.1 | D403,511 S | 1/1999 | Serbinski ..................... D4/108 |
| 5,353,460 A | 10/1994 | Bauman ...................... 15/22.1 | 5,855,216 A | 1/1999 | Robinson .................... 132/322 |
| 5,354,246 A | 10/1994 | Gotman ....................... 475/248 | 5,862,558 A | 1/1999 | Hilfinger et al. ................ 15/28 |
| 5,355,638 A | 10/1994 | Hoffman ....................... 451/32 | | | |

| | | | | | | |
|---|---|---|---|---|---|---|
| 5,864,915 A | 2/1999 | Ra .................... 15/167.1 | DE | 35 12 190 A1 | 10/1986 |
| 5,867,856 A | 2/1999 | Herzog .................... 15/22.4 | DE | 8626725 | 5/1987 |
| 5,896,615 A | 4/1999 | Zaksenberg .................... 15/167.1 | DE | 37 36 308 A1 | 7/1989 |
| 5,899,693 A | 5/1999 | Himeno et al. .................... 433/119 | DE | 41 42 404 C2 | 7/1991 |
| D410,787 S | 6/1999 | Barre et al. .................... D4/104 | DE | 40 03 305 A1 | 8/1991 |
| 5,908,038 A | 6/1999 | Bennett .................... 132/308 | DE | 42 23 195 A1 | 1/1994 |
| 5,927,300 A | 7/1999 | Boland et al. .................... 132/322 | DE | 42 23 196 A1 | 1/1994 |
| 5,927,976 A * | 7/1999 | Wu .................... 433/82 | DE | 42 26 659 A1 | 2/1994 |
| 5,930,858 A | 8/1999 | Jung .................... 15/22.1 | DE | 43 09 078 A1 | 9/1994 |
| 5,931,170 A | 8/1999 | Wu .................... 132/322 | DE | 297 15 234 U1 | 12/1997 |
| 5,943,723 A | 8/1999 | Hilfinger et al. .................... 15/22.1 | EP | 0 354 352 A1 | 2/1990 |
| 5,944,033 A | 8/1999 | Robinson .................... 132/322 | EP | 661 025 B1 | 7/1995 |
| D414,937 S | 10/1999 | Cornu et al. .................... D4/104 | FR | 429447 | 9/1911 |
| D414,939 S | 10/1999 | Pedro, Jr. et al. .................... D4/104 | FR | 1171337 | 1/1959 |
| 5,974,613 A | 11/1999 | Herzog .................... 15/22.1 | GB | 477799 | 1/1938 |
| 5,974,615 A | 11/1999 | Schwarz-Hartmann et al. .................... 15/22.4 | GB | 500517 | 2/1939 |
| | | | GB | 899618 | 6/1962 |
| 5,987,681 A | 11/1999 | Hahn et al. .................... 15/22.1 | GB | 1583558 | 8/1977 |
| 5,991,957 A | 11/1999 | Watanabe .................... 15/167.1 | GB | 2175494 | 12/1986 |
| D417,960 S | 12/1999 | Moskovich et al. .................... D4/104 | JP | 53-33753 | 3/1978 |
| 6,000,083 A | 12/1999 | Blaustein et al. .................... 15/28 | JP | 403-222905 A | 10/1991 |
| 6,009,589 A | 1/2000 | Driesen et al. .................... 15/167.1 | SE | 324221 | 5/1970 |
| 6,021,538 A | 2/2000 | Kressner et al. .................... 15/28 | WO | WO 91/13570 | 9/1991 |
| 6,032,313 A | 3/2000 | Tsang .................... 15/22.1 | WO | WO 91/19437 | 12/1991 |
| 6,035,476 A | 3/2000 | Underwood et al. .................... 15/22.1 | WO | WO 92/10146 | 6/1992 |
| D423,784 S | 5/2000 | Joulin .................... D4/104 | WO | WO 92/16160 | 10/1992 |
| 6,065,176 A | 5/2000 | Watanabe et al. .................... 15/167.1 | WO | WO 93/10721 | 6/1993 |
| 6,095,811 A | 8/2000 | Stearns .................... 433/29 | WO | WO 93/15628 | 8/1993 |
| 6,165,131 A | 12/2000 | Cuse et al. .................... 600/495 | WO | WO 94/04093 | 3/1994 |
| 6,183,254 B1 | 2/2001 | Cohen .................... 433/92 | WO | WO 94/26144 | 11/1994 |
| 6,299,444 B1 | 10/2001 | Cohen .................... 433/91 | WO | WO 95/02375 | 1/1995 |
| 6,349,442 B1 | 2/2002 | Cohen et al. .................... 15/22.1 | WO | WO 95/33419 | 12/1995 |
| | | | WO | WO 01/28452 | 4/2001 |
| | FOREIGN PATENT DOCUMENTS | | WO | WO 01/28452 A1 | 4/2001 |
| DE | 17 66 651 C2 | 12/1981 | WO | WO 01/45582 A1 | 6/2001 |
| DE | 3431481 A1 | 2/1986 | | | |

* cited by examiner

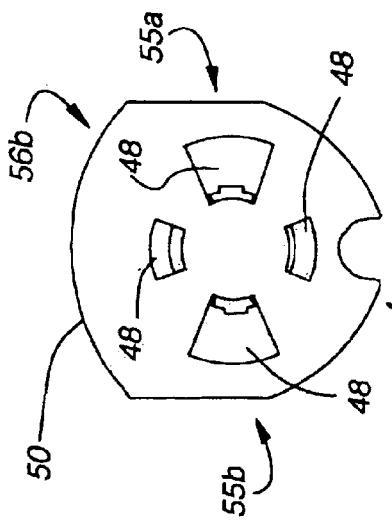
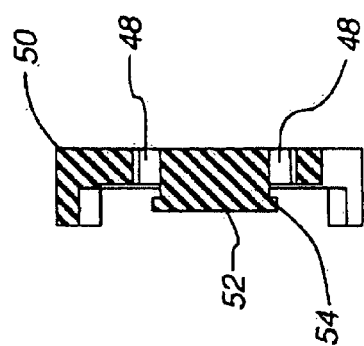
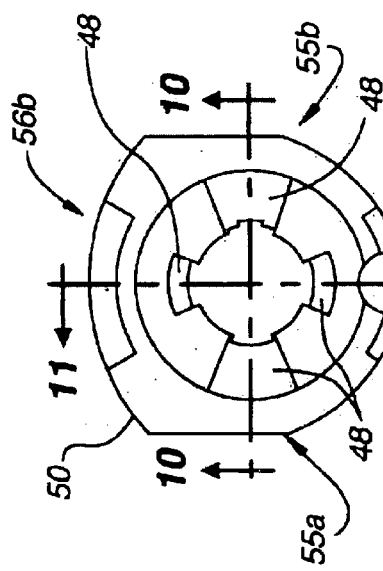
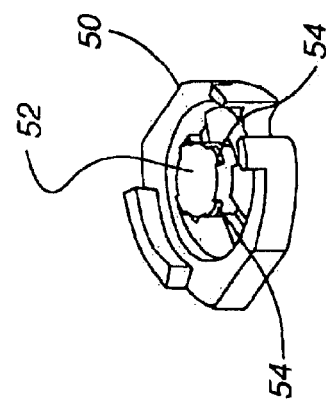
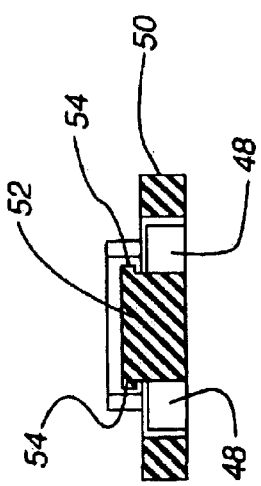

EXAMPLE OF BRISTLE MOTION: SECONDARY MOTOR OPERATING

EXAMPLE OF BRISTLE MOTION: PRIMARY MOTOR OPERATING
& SECONDARY MOTOR OPERATING

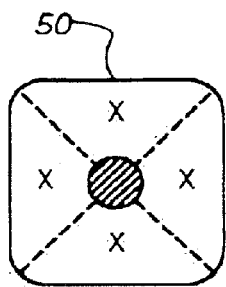
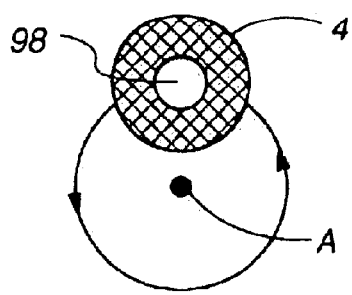
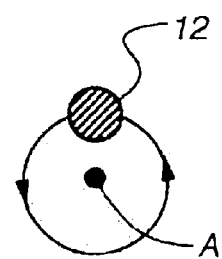
*Fig. 25A*  *Fig. 25B*  *Fig. 25C*
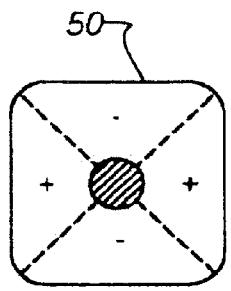
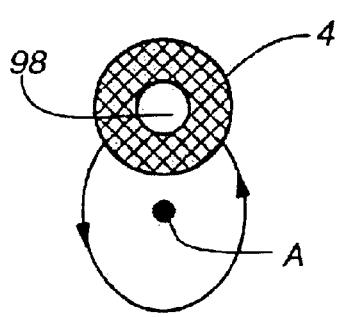
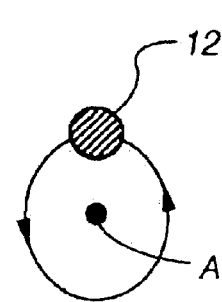
*Fig. 26A*  *Fig. 26B*  *Fig. 26C*
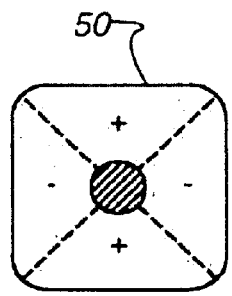
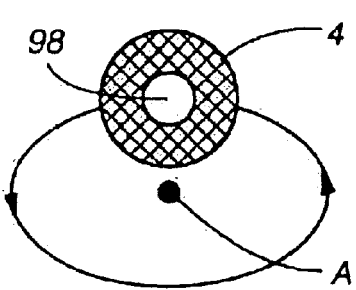
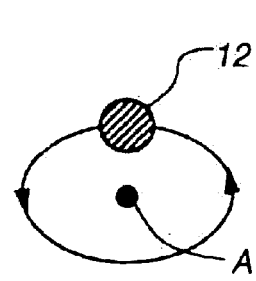
*Fig. 27A*  *Fig. 27B*  *Fig. 27C*
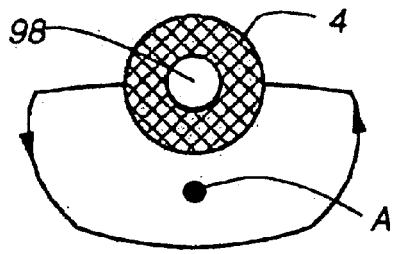
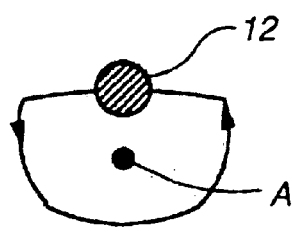
*Fig. 28A*  *Fig. 28B*

DUAL MOTOR ORAL HYGIENE DEVICE

CROSS REFERENCES TO RELATED APPLICATIONS

This application claims priority to commonly owned U.S. provisional application No. 60/305,413, filed Jul. 12, 2001, and U.S. provisional application No. 60/347,577, filed Jan. 11, 2002, the disclosures of which are hereby incorporated herein by reference in their entirety.

BACKGROUND OF THE INVENTION

1. Field of the Invention

This invention relates to a powered oral hygiene device having at least two motors to vibrate the device head.

2. Description of Related Art

Typically, electric oral hygiene devices such as electric toothbrushes include a single motor which drives a motion-creating mechanism, which in turn causes the head of the device to move during use. Such motion, commonly in the form of linear reciprocation, rotation or oscillation, enhances the cleaning of one's teeth. Because a typical electric toothbrush includes only a single motor, the automatic motions of the electric toothbrush are generally limited.

As recognized by the present inventors, there is a need for an oral hygiene device having complex vibrations or movements at the head of the oral hygiene device to provide a useful cleaning or polishing effect for teeth.

It is against this background that various embodiments of the present invention were developed. The features, utilities and advantages of the various embodiments of the invention will be apparent from the following more particular description of embodiments of the invention as illustrated in the accompanying drawings.

SUMMARY OF THE INVENTION

Disclosed herein are various embodiments of an oral hygiene device, each having at least two motors to simultaneously vibrate or impart motion upon the head portion of the oral hygiene device, most beneficially at the tip. In one embodiment, a first motor is positioned in the handle portion of the oral hygiene device to impart a first frequency of movement to the tip of the oral hygiene device, and a second motor is located in a head portion, generally in a shaft or an oral hygiene attachment to the oral hygiene device, to impart at least a second frequency of movement onto the tip of the device. When both the first and second motors are activated, the resulting movement of the tip of the oral hygiene device may include complex, substantially random movements, depending in part on the frequencies at which the motors are operating. In one embodiment described herein off-center or "eccentric" weight motors mounted at different locations in the handle portion and head portion are used to create vibrational movement of the tip, with the specific movement of the tip being substantially random or chaotic.

As used herein, the term "movement" encompasses the movement of the tip of a single member, for example, a flosser tip, or the tip of a bristle in a group of bristles, or the tips of a group of bristles as a whole, or the operating end of any other attachment. It can also relate to the movement of the base portion of the particular tip attached to the device, such as the base of the flosser tip, which may move differently than the tip of the flosser due to the physical characteristics of the flosser itself (e.g., length, shape, material, and flexing characteristics). The types of movement contemplated by the present invention may include: translational (e.g., as a wiper blade on a car windshield); rotational (about a longitudinal axis, e.g., the motion of a drill bit, either continuously clockwise or counterclockwise or alternating clockwise and counterclockwise); oscillatory (back and forth along the same path); pivotal (about a single pivot point, or other structure allowing pivotal movement in many planes); and orbital motion (such as a tip translating around a center point to form a closed loop path), or any combination thereof. These types of movements may be reciprocating (back and forth, in and out, up and down), oscillating, or any type of generally vibrating characteristic. The terms "vibration," "vibratory," or "vibrational" as used herein are meant to encompass any of the movements effected upon the oral hygiene device described above.

The movement of the head portion can take place in a single plane or in multiple planes. The movement of the various oral hygiene attachments used with the inventive oral hygiene device can be controlled, for example, by the position, orientation, and type of drive motor(s), associated drive linkage, the interaction between the motors and the housing, positioning structures, and dampening structures. A vibration focusing structure, for example, a rubber or elastomer mounting structure holding a motor in place, may be tuned to direct or dampen the movement of the head portion in particular directions. A pivot point constraining the shaft may also affect the movement of the head portion.

Different oral hygiene accessories may be attached to the oral hygiene device for use in oral hygiene, for example, a toothbrush head, a flosser tip (composed of either a single filament or a plurality of filaments), a tongue cleaner/scraper, a prophy cup for polishing, or other oral hygiene accessories. Further, a base unit may be provided for storing and charging the oral hygiene device, as well as for conveniently storing the various dental accessories for use with the oral hygiene device.

In one aspect of the invention, a power oral hygiene device is disclosed having a main body with a handle portion and a head portion. A first vibratory means is positioned in the handle portion and a second vibratory means is positioned in the head portion. The oral hygiene device also has a power means for providing energy to the first vibratory means and the second vibratory means.

In another aspect of the invention, a power oral hygiene device with a first motor operating at a first frequency and a second motor operating at a second frequency is disclosed. The oral hygiene device has a power source for providing energy to operate the first motor and the second motor. The motors are selected such that a ratio of the first frequency generated by the first motor to the second frequency generated by the second motor is between 1.3 and 3.

Yet another embodiment of the invention disclosed is a power toothbrush having a main body with a handle portion and a head portion. A first vibratory motor positioned in the handle portion and a second vibratory motor positioned in the head portion. A power source is provided for providing energy to the first motor and the second motor.

A base unit for holding oral hygiene device is also disclosed. The base unit is composed of a carousel with a plurality of chambers and a carousel cover, which is positioned over and covers the carousel. A means for rotating the carousel underneath the carousel cover is also provided. The carousel cover has an outer surface containing an opening. Access to the chambers in the carousel is provided through the opening in the carousel cover. A portion of the carousel is also exposed through the opening in the carousel cover, allowing a user to engage and rotate the carousel.

In a further aspect of the invention, a tongue scraper is disclosed. The tongue scraper has a head with a first plurality of teeth arranged in a first row and a second plurality of teeth arranged in a second row, spaced apart from the first row. Each tooth in the first row is separated from adjacent teeth by a notch. Similarly, each tooth in the second row is separated from adjacent teeth by a notch. Each of the notches between the teeth in the first row is positioned directly opposite at least a portion of one of the teeth in the second row. In this manner, no part of a user's tongue is left unscraped when the tongue scraper is pulled in a straight line across the user's tongue.

Other features, utilities and advantages of various embodiments of the invention will be apparent from the following more particular description of embodiments of the invention as illustrated in the accompanying drawings and defined in the appended claims.

BRIEF DESCRIPTION OF THE DRAWINGS

FIG. 8 illustrates an isometric view of a motor mount in accordance with one embodiment of the present invention.

FIG. 9 illustrates a top view of a motor mount in accordance with one embodiment of the present invention.

FIG. 10 illustrates a sectional view of the motor mount of FIG. 9 in accordance with one embodiment of the present invention.

FIG. 11 illustrates a sectional view of the motor mount of FIG. 9 in accordance with one embodiment of the present invention.

FIG. 12 illustrates a bottom view of a motor mount in accordance with one embodiment of the present invention.

FIGS. 25A–C illustrate a motor mount with a first set of compression properties and the resulting impact of the motor mount on the movement of the base end and shaft of the motor frame in accordance with one embodiment of the present invention.

FIGS. 26A–C illustrate a motor mount with a second set of compression properties and the resulting impact of the motor mount on the movement of the base end and shaft of the motor frame in accordance with one embodiment of the present invention.

FIGS. 27A–C illustrate a motor mount with a third set of compression properties and the resulting impact of the motor mount on the movement of the base end and shaft of the motor frame in accordance with one embodiment of the present invention.

FIGS. 28A–B illustrate the movement of the base end and shaft of a motor frame resulting from a gap between the motor frame and the housing of an oral hygiene device in accordance with one embodiment of the present invention.

DETAILED DESCRIPTION OF THE INVENTION

The structures and functions of various embodiments of an oral hygiene device will now be described.

Structure of the Oral Hygiene Device

Figure 1:
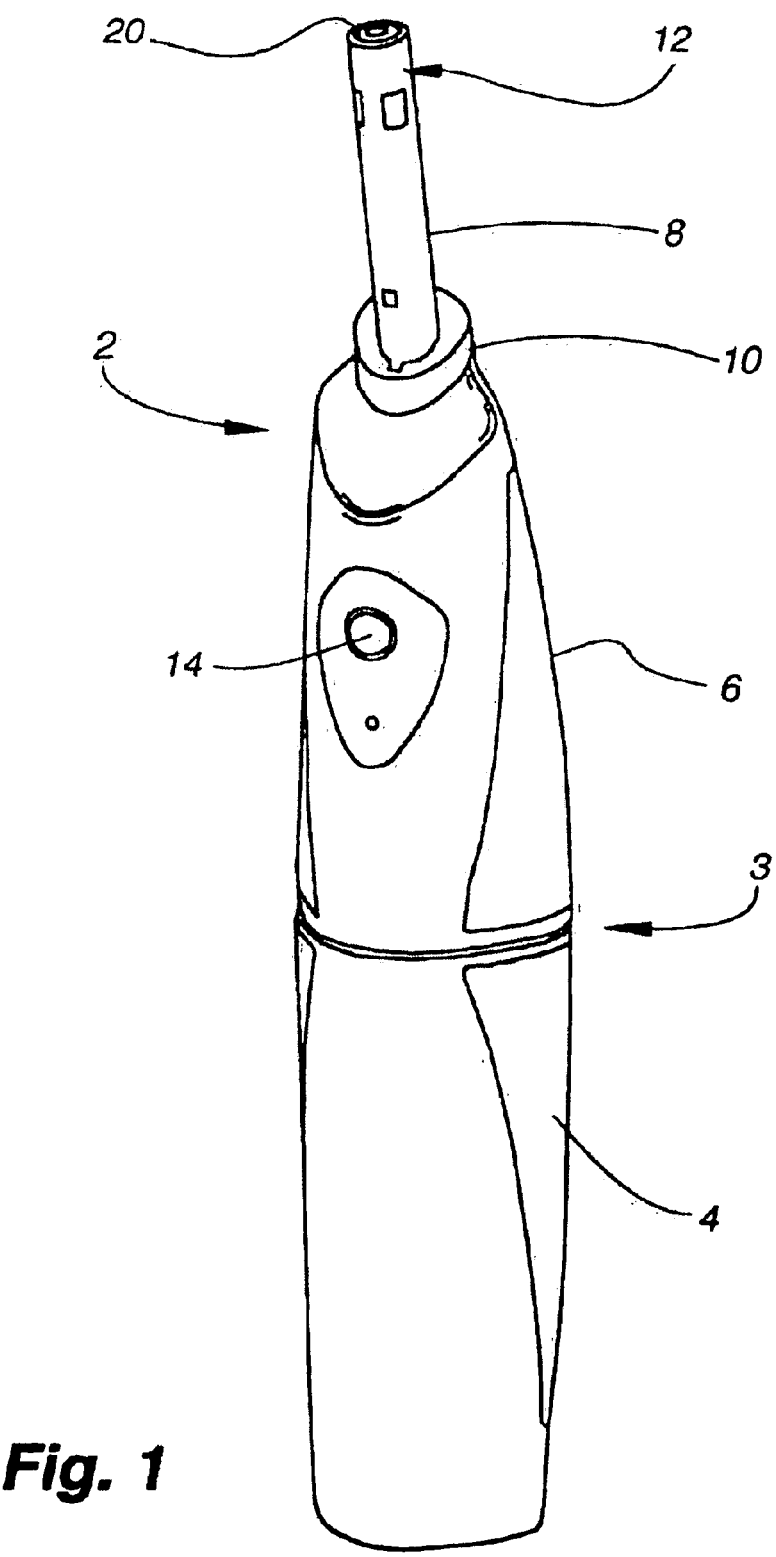
FIG. 1 illustrates an isometric view of an oral hygiene device in accordance with one embodiment of the present invention.
Figure 4:
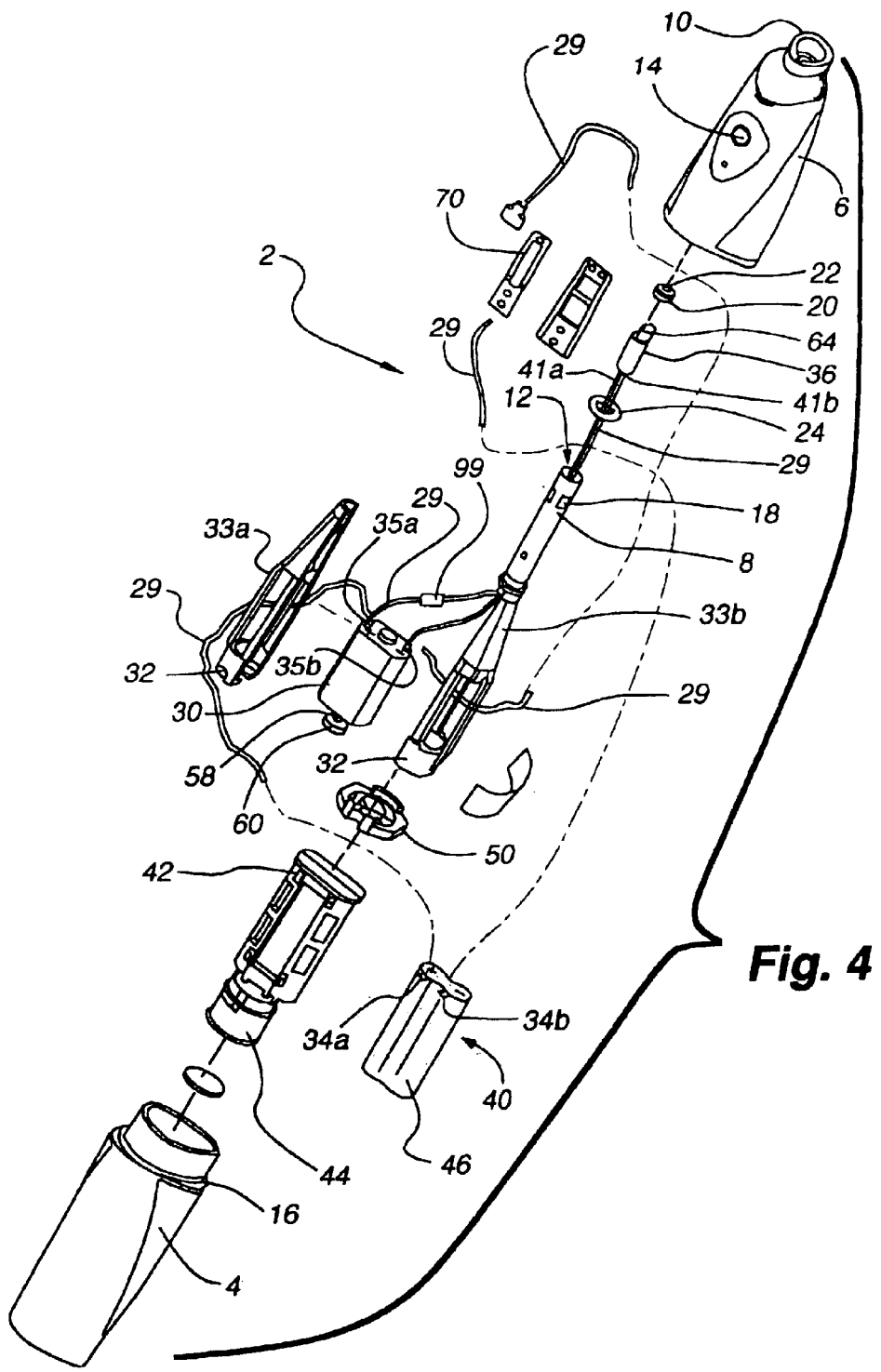
FIG. 4 illustrates an exploded view of an oral hygiene device in accordance with one embodiment of the present invention.

Referring to FIG. 1, an oral hygiene device 2 has a handle housing 3 composed of a lower handle housing 4 portion and an upper handle housing 6 portion, which form a body for the oral hygiene device 2. The upper handle housing 6 of the oral hygiene device 2 is adapted to securely fit about the mounting rim 16 of the lower handle housing 4 (as shown in FIG. 4).

Figure 5:
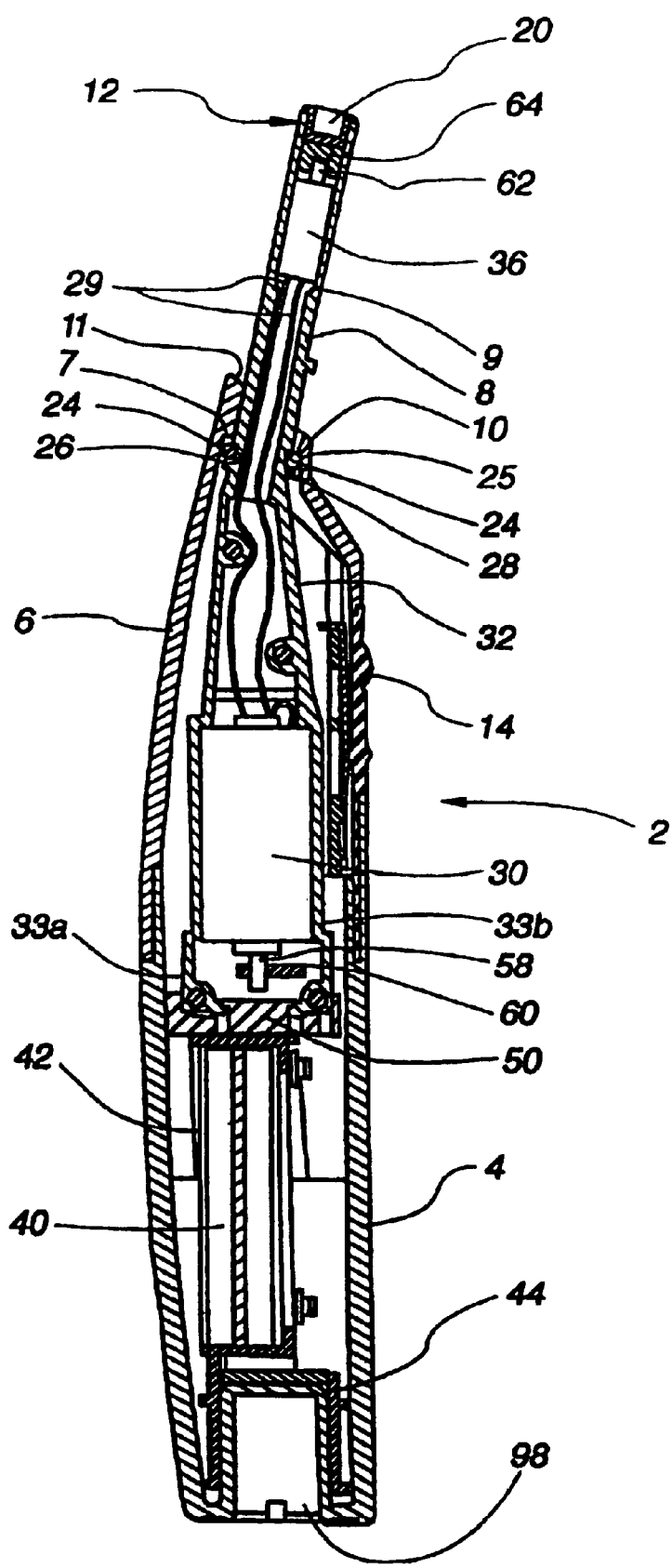
FIG. 5 illustrates a sectional view of an oral hygiene device in accordance with one embodiment of the present invention.

A shaft 8 extends from a ported nose portion 10 of the upper handle housing 6, and the shaft 8 has a tip 12 to which various oral hygiene attachments 250 (see FIGS. 20–23A) can be removably secured. As shown in FIGS. 1 and 5, the ported nose portion 10 of the upper handle housing 6 forms a positioning sleeve for providing a desired relation between the upper handle housing 6 and the tip 12 of the shaft 8. As will be described in greater detail below, the oral hygiene device 2 has, in one embodiment, a primary motor 30 and a secondary motor 36, each operating at a different frequency to generate movement and vibration of the shaft tip 12 to provide for dental cleaning when used with the various oral hygiene attachments 250.

In order to achieve the desired vibration and movement of the shaft 8, the motors 30, 36 may be eccentrically weighted (i.e., a mass is mounted off-center on a motor shaft). The vibration caused by an eccentric weight motor is generally characterized by an orbital type of movement. The motor shaft may turn rotationally in one direction (e.g., clockwise or counter clockwise) or oscillate back and forth to create the orbital vibration. Other vibrational motors or devices that cause vibration, for example, piezo electric vibrational devices and motors creating axial, linear, or oscillatory vibration, are likewise contemplated for use in this invention.

The upper handle housing 6 has on its outer surface a pad or button 14 for receiving depressions by a thumb or a finger of a user of the oral hygiene device 2. As will be explained below, depending upon the implementation, when the user depresses the button 14, a switch 70 closes and power is applied to both motors 30, 36 so that the motors 30, 36 impart various vibratory frequencies to the tip 12 of the oral hygiene device 2. The switch 70 may allow the user to actuate either the primary motor 30 motor in the handle housing 3, the secondary motor 36 in the shaft 8, a combination of both, or even to alter the speed at which the motors 30, 36 operate.

Figures 2, 3:
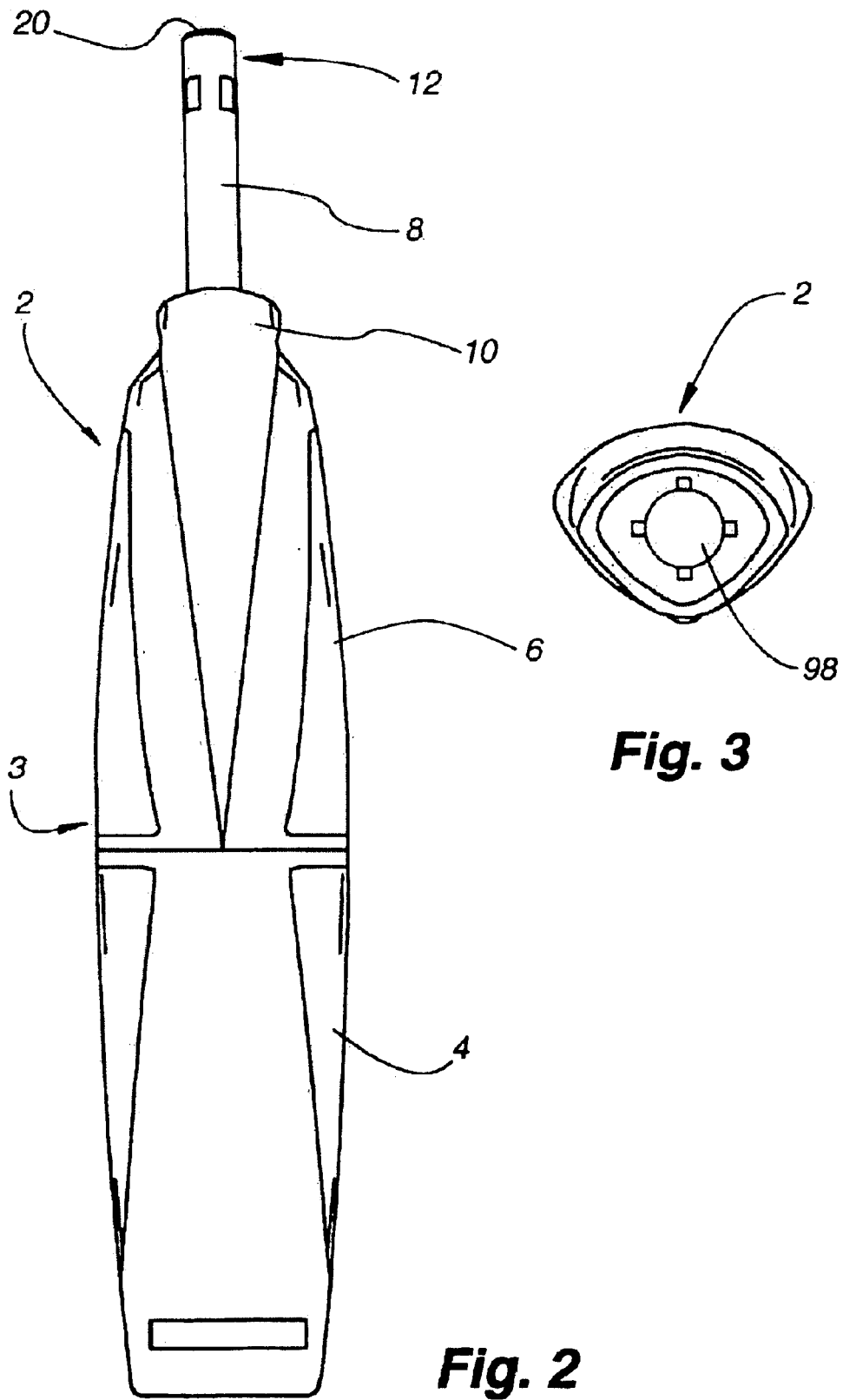
FIG. 2 illustrates a back side view of an oral hygiene device in accordance with one embodiment of the present invention.
FIG. 3 illustrates a bottom view of an oral hygiene device in accordance with one embodiment of the present invention.
Figure 15:
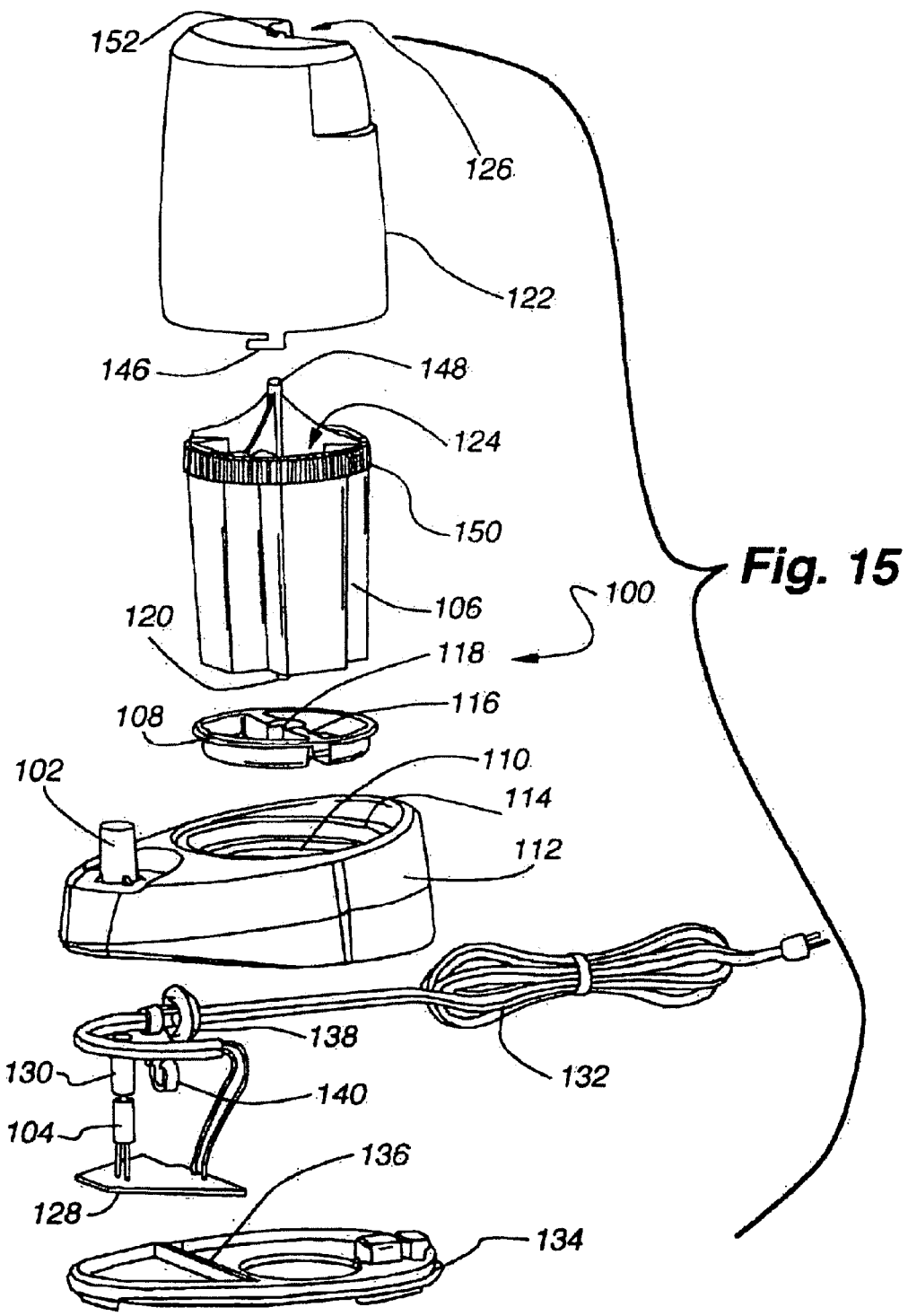
FIG. 15 illustrates an exploded view of a charging base for an oral hygiene device in accordance with one embodiment of the present invention.

Referring to FIG. 3, the oral hygiene device 2 has on its bottom end in the lower handle housing 4 a cavity 98 for capturing a post 102 of a charging unit 100 (as shown in FIG. 15) so that the oral hygiene device 2 can be stored and recharged if needed. The post capturing cavity 98 receives the post 102 to removably secure the oral hygiene device 2 on the charging unit 100.

Now referring to FIG. 4, an exploded view of an oral hygiene device 2 is shown in accordance with one embodiment of the present invention. A rechargeable battery 40 is positioned within a battery bracket 42 having a coil/magnet 44 combination attached thereto that can be used for charging the rechargeable battery 40, for example, when the oral hygiene device 2 is positioned within a charging unit 100 (as shown in FIG. 15). The coil/magnet 44, battery bracket 42, and battery 40 may be positioned substantially within the lower handle housing 4 of the oral hygiene device 2.

Figure 6:
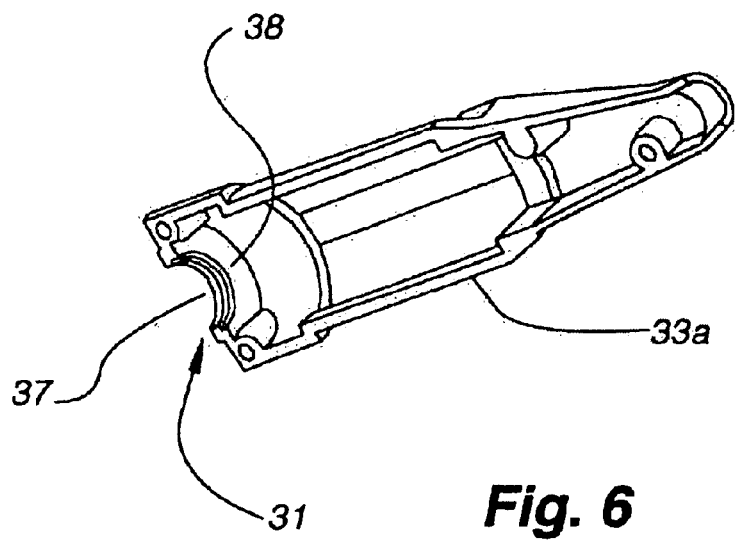
FIG. 6 illustrates an isometric view of a portion of a motor frame in accordance with one embodiment of the present invention.
Figure 7:
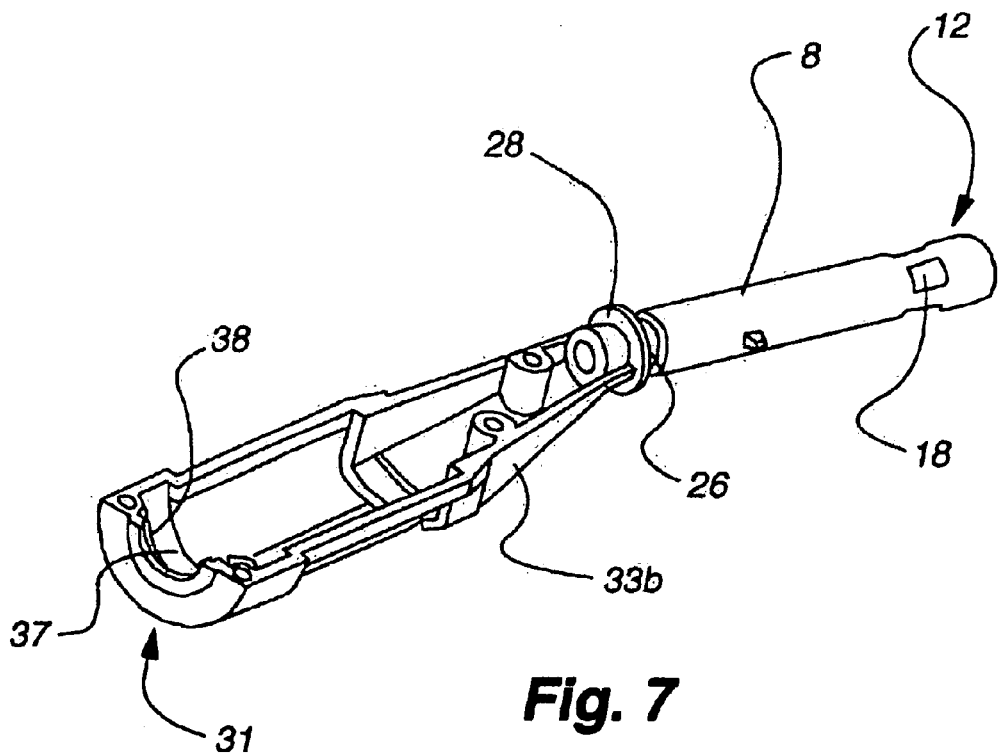
FIG. 7 illustrates an isometric view of a portion of a motor frame having a shaft in accordance with one embodiment of the present invention.

The primary motor 30 may be positioned within a motor frame 32, as shown in FIG. 4. In one embodiment, the motor frame 32 is a two-piece structure (as shown in FIGS. 4, 6, and 7), which has a first motor housing portion 33a that is secured to a second motor housing portion 33b. The second motor housing portion 33b is attached to or formed integrally with the shaft 8, whereby the shaft 8 is actually part of the motor frame 32. The two-piece motor frame 32 snugly secures the primary motor 30 into a position within the motor frame 32. Therefore, when the primary motor 30 is activated, the vibratory force generated by the primary motor 30 is imparted to the motor frame 32, and thereby to the shaft 8. Both the first and second motor housing portions 33a and 33b of the motor frame 32 may be slotted along a portion of each side so that the wires 29 from the battery 40 may be connected to the primary motor 30 and further to the secondary motor 36 within the motor frame 32.

The shaft 8 may be integral with the motor frame 32 and outwardly protrude from the ported nose portion 10 of the upper handle housing 6. The shaft 8 of the motor frame 32 is generally cylindrical and receives the secondary motor 36 and the wires 29 within the interior of the shaft 8. As shown in FIG. 5, the shaft 8 may have tapered interior walls 9 defining an expanding (semi-conical) cylindrical cavity towards the tip 12 of the shaft 8, and an annular shoulder 11 interior to the shaft 8 to maintain the secondary motor 36 axially in position within the interior of the shaft 8. Similar to the action of the primary motor 30, the secondary motor 36 when activated imparts a vibratory force to the shaft 8 in which the secondary motor 36 is constrained. The vibrational force imparted by the secondary motor 36 to the tip 12 of the shaft 8 may be more vigorous than the force imparted by the primary motor 30 due to the proximity of the secondary motor 6 to the tip 12. An end cap 20 is inserted into the open end of the shaft tip 12 in order to provide a fluid-tight seal to preferably prevent fluids or other matter from entering the shaft tip 12 once the secondary motor 36 is positioned within the shaft 8.

Typically, due to space limitations, the primary motor 30 will be larger than the secondary motor 36. Given the structure of the oral hygiene device 2, as shown in FIG. 7, it is contemplated that the secondary motor 36 will generate vibrational energy with a higher frequency and lower amplitude than the primary motor 30, which would generate vibrational energy with a relatively lower frequency and higher amplitude than the secondary motor 36. However, the oral hygiene device 2 could be constructed with the primary motor 30 of a higher frequency and lower amplitude than the secondary motor 36, a higher frequency and higher amplitude than the secondary motor 36, a lower frequency and lower amplitude than the secondary motor 36, or both motors 30, 36 could have identical vibrational frequencies and amplitudes as desired. The selection of the vibrational frequency and the amplitude may be made to maximize the effectiveness of the cleaning motion of the tip 12 and the oral hygiene attachment 250. Depending upon the type of oral hygiene attachment 250, achieving a desired level of effectiveness might require different combinations of motor placement, for example, placing both the primary motor 30 and the secondary motor 36 in the handle housing 3, placing both motors 30, 36 in the shaft 8, placing the primary motor 30 in the shaft 8 and the secondary motor 36 in a oral hygiene attachment 250, or placing the primary motor 30 in the handle housing 3 and the secondary motor 36 in a oral hygiene attachment 250.

An O-ring 24 is positioned within an annular channel 26 (as shown in FIG. 7) of the shaft 8. As shown in FIG. 5, when the motor frame 32 with the integral shaft 8 is positioned within the upper handle housing 6, the O-ring 24 is circumferentially constrained and may be compressed between an annular backplate 28 of the shaft 8 and an annular sealing shoulder 7 defined on the interior of the upper handle housing 6. The O-ring 24 may be made of silicone having a Shore hardness of approximately 40. The O-ring 24 is water resistant so that when secured around the shaft 8 and positioned within the upper handle housing 6, a fluid tight seal is formed which helps prevent water from entering into the cavity of the oral hygiene device 2.

The point of intersection between the O-ring 24, the annular backplate 28, and the annular sealing shoulder 7 may act as a circumferential pivot point 25 (i.e., pivoting may occur about more than one pivot axis) about which the vibration of the motor frame 32 is translated into vibration of the shaft 8, and thus the tip 12 and any oral hygiene attachment 250 attached thereto. In some embodiments, the O-ring 24 may serve to isolate the vibrations of the secondary motor 36 from the handle housing 3, of the oral hygiene device 2. In one embodiment, the primary motor 30 and the secondary motor 36 are positioned at opposing ends of the motor frame 32 structure, as shown in FIG. 5. The motors 30, 36 may further be oriented so that the eccentric weights 60, 64 of each motor 30, 36 are positioned away from the pivot point 25 to generate a greater amount of vibration about the tip 12 of the shaft 8. The O-ring 24 may also act as a spring that generates alternate vibratory frequencies and patterns in the oral hygiene device 2. The variations in the vibrational energy are caused by a "rebound" motion of the shaft 8 as it presses against the O-ring 24 and the interior of the upper handle housing 6 adjacent the O-ring 24. The compression and decompression of the O-ring 24 interacts with the vibration patterns of the motors 30, 36 and causes additionally complex vibration patterns within the oral hygiene device 2.

At the base end 31 of the motor frame 32 proximate the primary motor 30, a motor mount 50 or anchor may be attached to the base end 31 of the motor frame. The motor mount 50 may be provided in order to selectively regulate the movement of the primary motor 30 as it moves within the interior cavity of the oral hygiene device 2. The motor mount 50 is designed to fit tightly or snugly within the lower handle housing 4 of the oral hygiene device 2 (see FIG. 5). The cross-section of the motor mount 50 is sized to substantially match the interior cross-sectional shape of the lower handle housing 4 within and against which the motor mount 50 fits. The motor mount 50 also may dampen or isolate the vibrations of the primary motor 30 so as to reduce vibrations translated to the handle housing 3. Co-pending, co-owned U.S. application Ser. No. 10/045,953, entitled TOOTHBRUSH WITH MOTOR INTEGRATED WITH VIBRATING HEAD, filed Jan. 12, 2002, provides additional details with respect to vibration isolation structures and its entire contents are hereby incorporated by reference in their entirety as if fully disclosed herein. The motor mount 50 may be made of rubber or any suitable elastomer. In one example, the motor mount 50 may be made of a styrene-ethylene butylene-styrene material of an approximate Shore hardness of 40.

Referring to FIGS. 8–12, the motor mount 50 may have a central protrusion 52 with tabs 54 adapted to be positioned within an opening 37 at the base end 31 of the motor frame 32 (as shown in FIG. 7). Once the central protrusion 52 of the motor mount 50 is positioned within the opening 37, the tabs 54 help to maintain the attachment between the motor mount 50 and the motor frame 32 by extending over a shelf 38 at the base end 31 of the motor frame 32. The motor frame 32 may have a cross-sectional shape that is smaller than that of the handle housing 3. By suspending the primary motor 30, and the motor frame 32 around it, within the handle housing 3 by the O-ring 24 on the shaft 8 of the motor frame 32 and the motor mount 50 at the base end 31 of the motor frame 32, the transfer of vibration from the primary motor 30 to the handle housing 3 is dampened.

When the primary motor 30 is positioned within the motor frame 32 and activated, the tendency of the primary motor 30 is to create a vibrational force causing the motor-frame 32 to revolve about the O-ring pivot point 25. In one embodiment, the motor mount 50 is designed to move the tip 12 in a generally elliptical pattern, as opposed to a circle, so that the tip 12 ultimately moves up and down a greater distance than side to side in an ellipse having its major axis extending parallel with the plane of the user's teeth. To encourage this motion, the motor mount 50 may be formed with parallel lateral edges 55a and 55b and a curved front edge 56a and a back edge 56b.

As used herein, the directions of movement of any components of the oral hygiene device 2, e.g., the motor mount 50, the shaft 8, and ultimately an oral hygiene attachment 250, are indicated with respect to the interface between the oral hygiene attachment 250 and a user's teeth. Therefore, "front" indicates the side of the oral hygiene device 2, and its components, parallel to the side of an oral hygiene attachment 250 that is designed to contact the user's teeth, e.g., the side with bristles 202 (see FIG. 20), a flosser tip 212a (see FIG. 21) or a prophy polishing cup 222 (see FIG. 22). "Back" indicates the side opposite the front side. "Lateral," "side-to-side," and "left" and "right" therefore indicate the sides adjacent to the front side as viewed from the front side.

In this embodiment, the curved front edge 56a and back edge 56b are, by design, less compressible and thus discourage motion of the primary motor 30 into and out of the plane of a user's teeth as the oral hygiene device 2 is used. By forming the front edge 56a and back edge 56b with a stiffer resilience, those portions of the motor mount 50 deform less under the force of the primary motor 30. In contrast, the parallel lateral edges 55a and 55b may be designed to provide less dampening than the front edge 56a and back edge 56b, thus permitting the primary motor 30 to move side-to-side (and up and down to a limited extent). This movement of the primary motor 30 allowed by the motor mount 50 defines a roughly elliptical path having a major axis extending substantially parallel with the plane of the user's teeth. In this embodiment, the motor mount 50 controls and limits the movement of the primary motor 30 and the motor frame 32 within the interior of the oral hygiene device 2 so that the resulting motion of the primary motor 30 and the motor frame 32 generally is elliptical. Because the motor frame 32 is connected with the shaft tip 12, the shaft tip 12 will also correspondingly move in a generally similar pattern. The stiffness of various areas of the motor mount 50 may be affected by its material properties, for example, the type of material used, the thickness of the material, and the form of the material, as well as structural restrictions formed in the lower handle housing 4.

It should be understood that the motor mount 50 shown herein is sized and shaped to promote a side-to-side motion of the primary motor 30, and the motor frame 32, and the shaft tip 12. However, a motor mount 50 of different size or shape may be used to impart a different fundamental motion on the shaft 8 of the oral hygiene device 2, for example, a circular motion, an elliptical motion with a major axis in a plane normal to or at another angle to the users teeth, a planar side-to-side translation pattern, a planar up-and-down pattern, or a planar in-and-out translation pattern.

Figure 24:
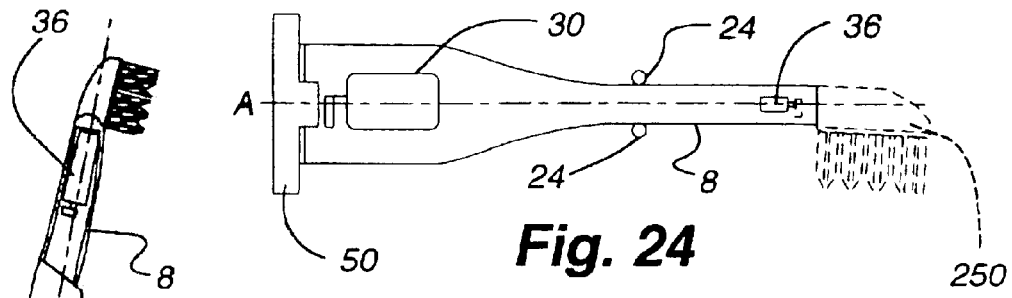
FIG. 24 illustrates a motor frame positioned along a longitudinal axis.

FIG. 24 shows a schematic of the motor frame 32 and the surrounding structure that affects the motion of the motor frame 32, and thus the various oral hygiene attachments 250 to the tip 12. The base end 31 of the motor frame 32 is attached to the motor mount 50. The mid portion of the housing is constrained about the circumferential pivot point 25 at the O-ring 24. The primary motor 30 is positioned in the motor frame 32 near its base end 31, with the eccentric weight 60 positioned as far toward the base end 31 as possible. A secondary motor 36 is positioned within the shaft 8 on the opposite end of the motor frame 32, with its eccentric weight 64 positioned as far toward the tip 12 as possible. The motor mount 50 is held in place by its interface with the motor frame 32 and the lower handle housing 4 (as shown in FIG. 5). The circumferential pivot point 25 is likewise held in place by its interface with the shaft 8 of the motor frame 32 and the upper handle housing 6.

When the primary motor 30 is actuated, the base end 30 of the motor frame 32 is urged to move in a rotational path. If the motor mount 50 is designed to apply a generally equal force to all sides of the motor frame 32 as indicated in FIG. 25A (the "x" in each of the exemplary sections of the motor mount 50 indicates the equivalence of the level of compressibility of each section), the movement of the base end 31 of the motor frame 32 will be generally circular as shown in FIG. 25B. Likewise, if the circumferential pivot point 25 is designed to apply a generally equal force to all sides of the shaft 8 of the motor frame 32, the movement of the tip 12 of the shaft 8 will also be generally circular as shown in FIG. 25C. The eccentric weight 60 of the primary motor 30 causes the base end 31 of the motor frame 32 to move in a rotational path, which in turn makes the tip 12 of the shaft 8 move in a rotational path. The motions depicted in FIGS. 25B, 25C, 26B, 26C, 27B, 27C, 28A, and 28B are exaggerated for explanatory purposes.

Assuming constant rotations per minute (RPM), location, and eccentric weight for the primary motor 30, the motion of the tip 12 can be adjusted by changing either the forces applied to the base end 31 of the motor frame 32, the circumferential pivot point 25, or both. For example, the lateral motion of the base end 31 and the tip 12 can be reduced by stiffening the material of the motor mount 50 adjacent to the lateral sides of the motor frame 32 relative to the material of the motor mount 50 adjacent to the front and back sides of the motor frame 32, as shown in FIG. 26A by the indication of "+" signs for areas of greater stiffness and "−" signs for areas of lesser rigidity (or by otherwise restricting the movement of the motor frame 32 in the side-to-side direction). The material of the motor mount 50 may be of varying consistency or varying substances in order to provide the variable elasticity desired. Alternatively, or additionally, apertures 48 or recesses may be formed in the motor mount 50 to remove some of the material forming the motor mount 50 and increasing its deformability in resistance to the forces imparted by the primary motor 30. As shown in FIGS. 26B and 26C, this configuration of the motor mount 50 would cause the motor frame 32 to follow a generally elliptical orbit with a major axis extending vertically relative to the circular paths shown in FIGS. 25B and 25C. (The paths described herein may not precisely be elliptical as technically defined, but may be any of a variety of oblong closed loops).

Additionally, the vertical motion of the base end 31 and the tip 12 can be reduced by stiffening the material of the motor mount 50 adjacent to the front and back of the motor frame 32 relative to the material of the motor mount 50 adjacent to the lateral sides of the motor frame 32, as shown in FIG. 27A by the indication of "+" signs for areas of greater stiffness and "−" signs for areas of lesser rigidity (or by otherwise restricting the movement of the motor housing in the up and down direction). As shown in FIGS. 27B and 27C, this configuration of the motor mount 50 would cause the motor frame 32 to follow a generally elliptical orbit with a major axis extending laterally relative to the circular paths shown in FIGS. 25B and 25C.

Further modification of the motion of the base end 31 or tip 12 may be made by further restricting the ability of the motor frame 32 to move, in any number of manners. For example, as shown in FIG. 5, the upper handle housing 6 engages the shaft 8 of the motor frame 32 at the ported nose portion 10 above the O-ring 24 (circumferential pivot point 25). A gap is formed between the shaft 8 of the motor frame 32 and the ported nose portion 10 of the upper handle housing 6 above the circumferential pivot point 25, toward the front side of the oral hygiene device 2. This configuration would restrain the motion of the base end 31 and the shaft 8 from movement in an upward direction (negating any flexure of the motor frame 32 between the pivot point 25 and the motor mount 50 attachment point), but would not restrain the shaft 8 from moving toward the front of the oral hygiene device 2. The resulting pattern of the movement of the base end 31 of the motor frame 32 and the tip 12 would be similar to the patterns shown in FIGS. 28A and 28B, respectively.

The pattern of motion of the tip 12 of the shaft 8 can be further modified by other adjustments to the physical surroundings of the motor frame 32. For example, the motor mount 50 could be designed to have differing compression characteristics on different sides (as opposed to symmetrical compression characteristics as described above). Further, hard physical restraints, for example, formed in the design of the lower handle housing 4 or upper handle housing 6, could be used to modify the motion as desired.

The movement of a tip of the oral hygiene attachment 250 actually attached to the oral hygiene device 2, for example, the tip of each bristle 202 on the toothbrush 200, or the tip of the single element flosser 212a, is defined by the structural relationship of the oral hygiene attachment 250 tip to the tip 12 of the shaft 8, and the physical characteristics of the oral hygiene attachment 250 tip. For example, with a toothbrush 200 attached to the shaft 8, each individual bristle 202 extends substantially normal to the front of the shaft 8. If the movement of the tip 12 of the shaft 8 is designed to be an elongated ellipse with a major axis extending parallel to the surface of the teeth, the tip of an individual bristle 202 on the toothbrush 200 will move substantially in a flat elliptical motion in the plane of the surface of the teeth. In effect, the bristle tip will move side-to-side a great deal more than it will move forward and backward (i.e., toward and away from the teeth).

In addition to this movement caused by the primary motor 30, the actuation of the secondary motor 36, positioned near the tip 12 of the shaft 8 imparts an additional movement characteristic to the tip 12 of the shaft 8 as well as the tip of the oral hygiene attachment 250 attached to the shaft 8. The characteristics of the secondary motor 36, for example, speed (frequency of rotation), eccentricity (weight of eccentric mass), and position in the oral hygiene device 2, affects the ultimate secondary motion imparted to the tip 12 of the shaft 8 and the tip of the oral hygiene attachment 250 attached to the shaft 8. This secondary motion, combined with the motion caused by the primary motor 30, creates a randomized movement of the tip 12 of the shaft 8, and the tip of the oral hygiene attachment 250 attached to the shaft tip 12. This randomized motion is described further herein with respect to FIGS. 18 and 19.

Figure 20:
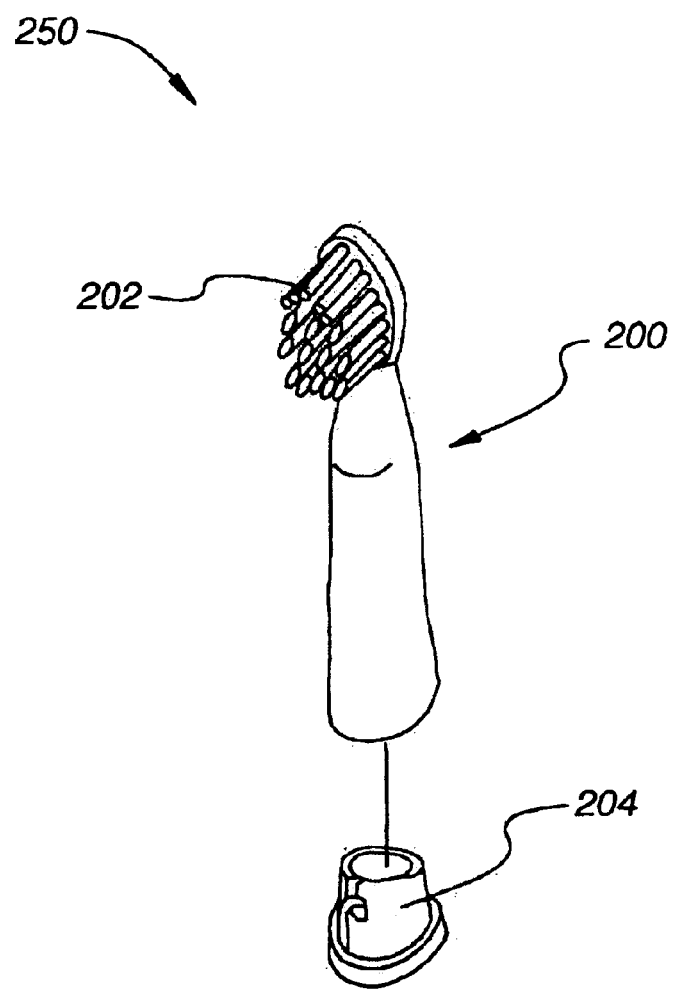
FIG. 20 illustrates an isometric view of a toothbrush attachment in accordance with one embodiment of the present invention.
Figure 21:
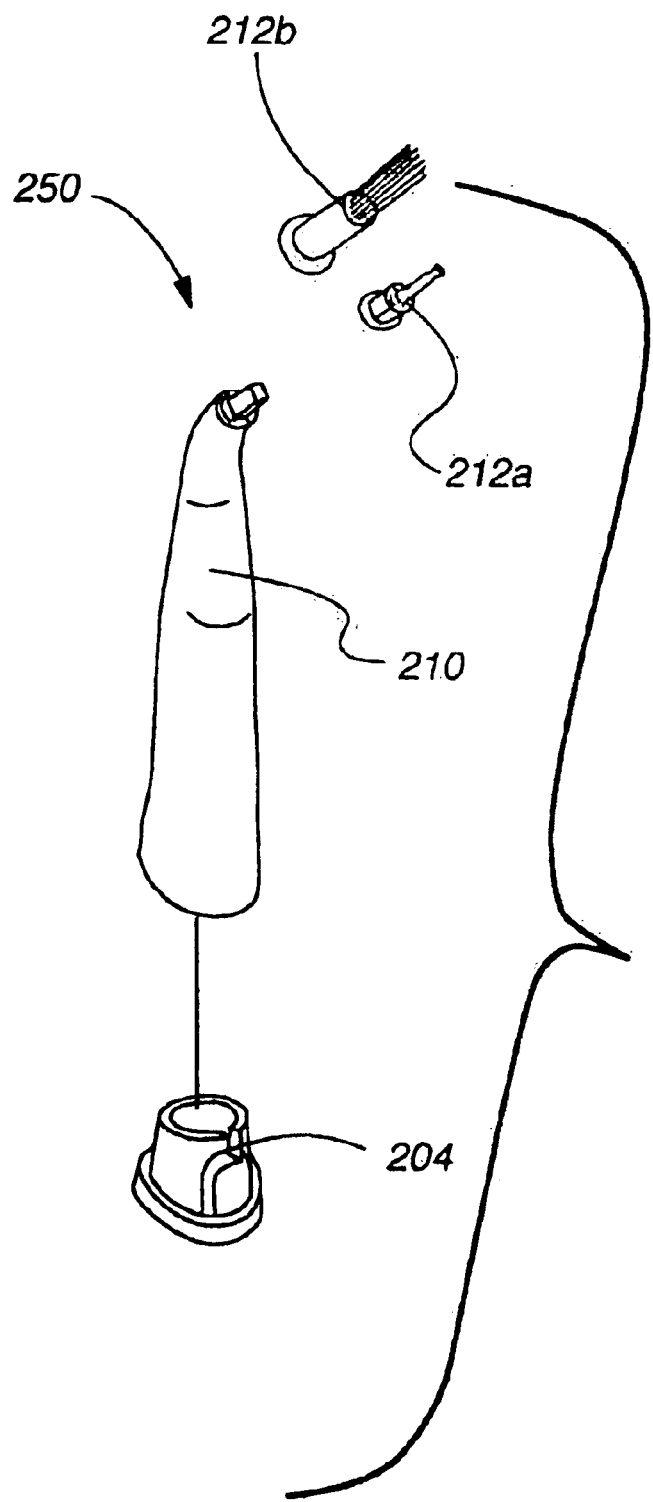
FIG. 21 illustrates an isometric view of a flosser tip/flosser head attachment in accordance with one embodiment of the present invention.

The tip 12 of the oral hygiene device 2 may be adapted to receive a plurality of different dental attachments. In this way, the oral hygiene device 2 can be used in different ways by a user to clean, polish, or otherwise service the user's teeth. For example, a brush head 200 having bristles 202 (as shown in FIG. 20) for brushing one's teeth may be connected with the end of the shaft 8 of the oral hygiene device 2. A flosser head 210 (having a flossing tip 212a with one filament or a flossing tip 212b with a plurality of filaments) (as shown in FIG. 21) may be connected with the end of the shaft 8 of the oral hygiene device 2 so that the user can floss with the oral hygiene device 2. Such flossing tips 212a, 212b are described in more detail in co-pending, co-owned application Ser. No. 09/883,013, TIP FOR DENTAL FLOSSING DEVICE, filed Jun. 15, 2001, which is hereby incorporated by reference in its entirety as if fully set forth herein.

Figure 22:
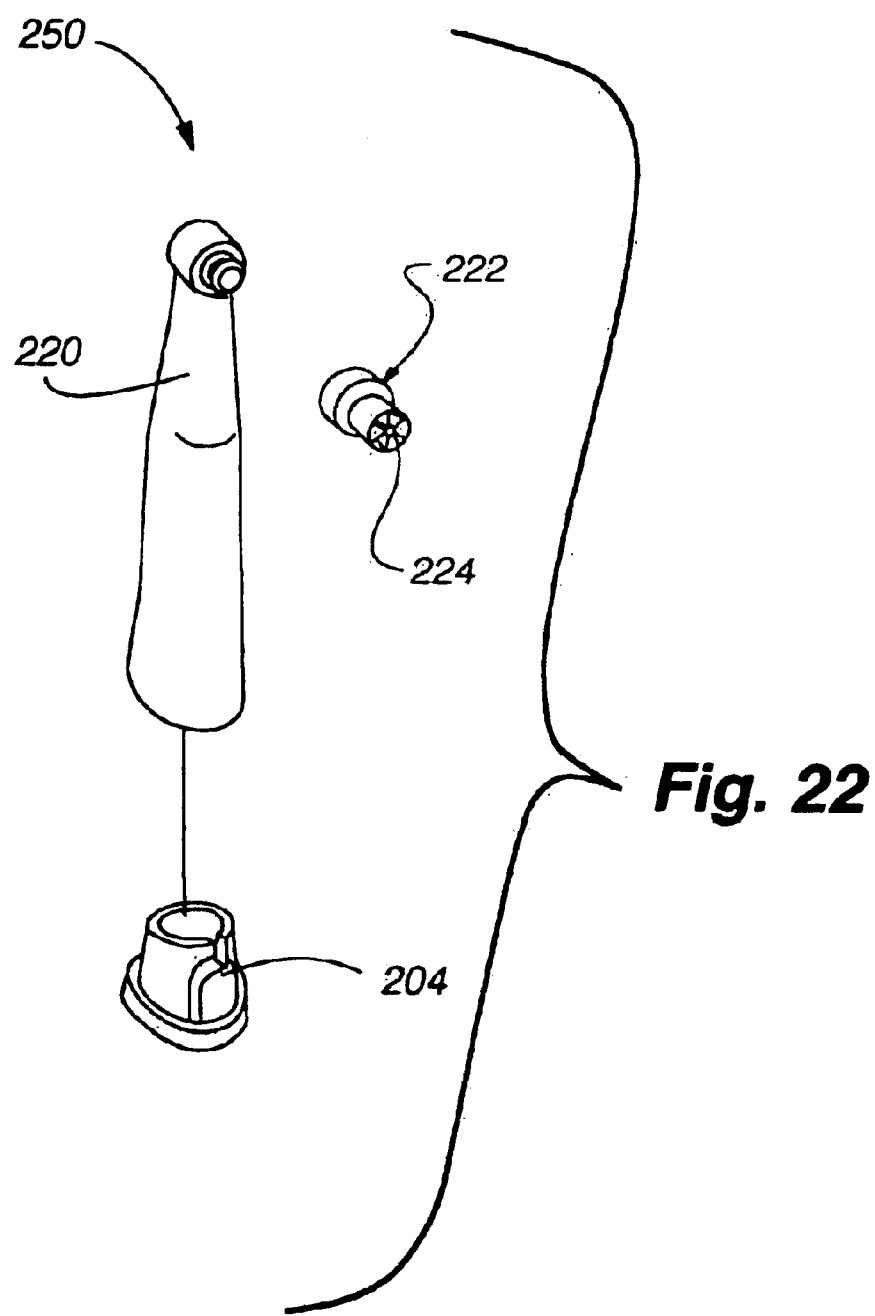
FIG. 22 illustrates an isometric view of a polishing cup head attachment in accordance with one embodiment of the present invention.

Alternatively, a polishing head 220 with a replaceable prophy polishing cup 222 (as shown in FIG. 22) can be connected with the end of the shaft 8 of the oral hygiene device 2, so that a user may polish teeth with the oral hygiene device 2. The prophy cup 222 includes a flexible cup-like head 224. During use, the cup-like head 224 is used to store dental paste for application to the user's teeth. The cup-like head 224 with paste is then pressed against the user's teeth to force the paste into the grooves, indentations, and spaces in and around the user's teeth. The cup-like head is flexible so as to ensure no damage or discomfort is brought to the user or their teeth during use.

Figure 23A:
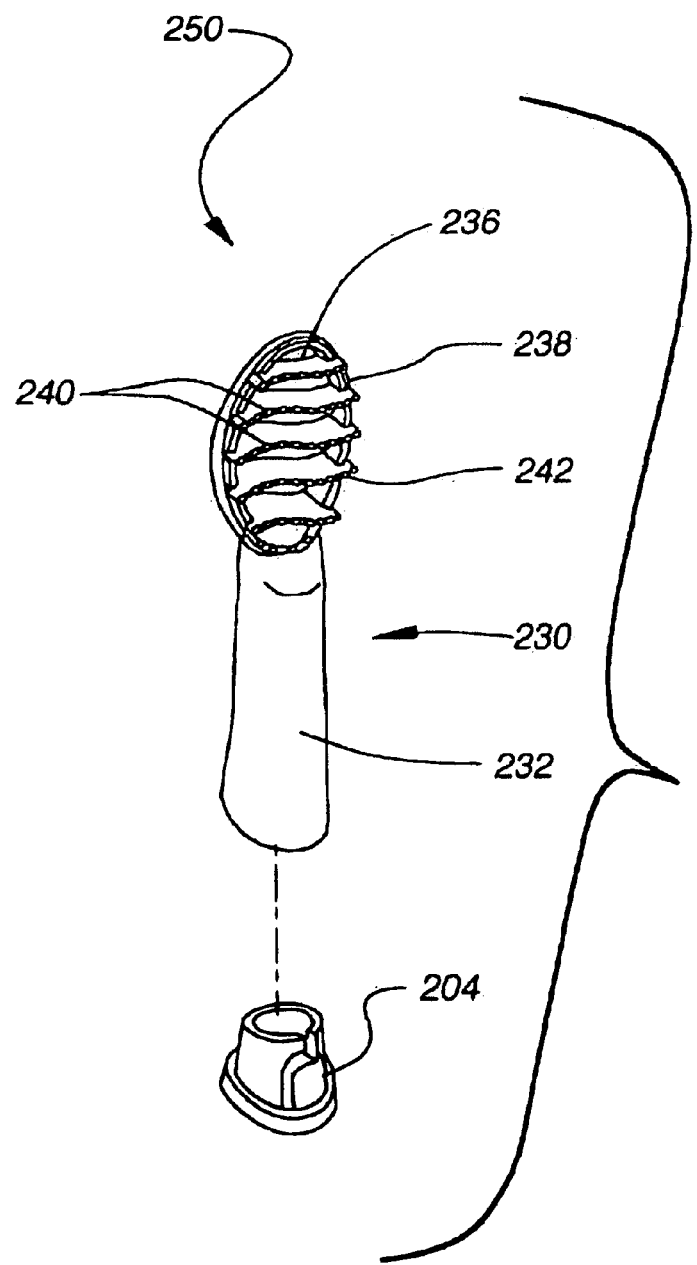
FIGS. 23A–H illustrate various views of a tongue cleaner attachment in accordance with one embodiment of the present invention.
Figures 23B, 23C, 23D, 23E:
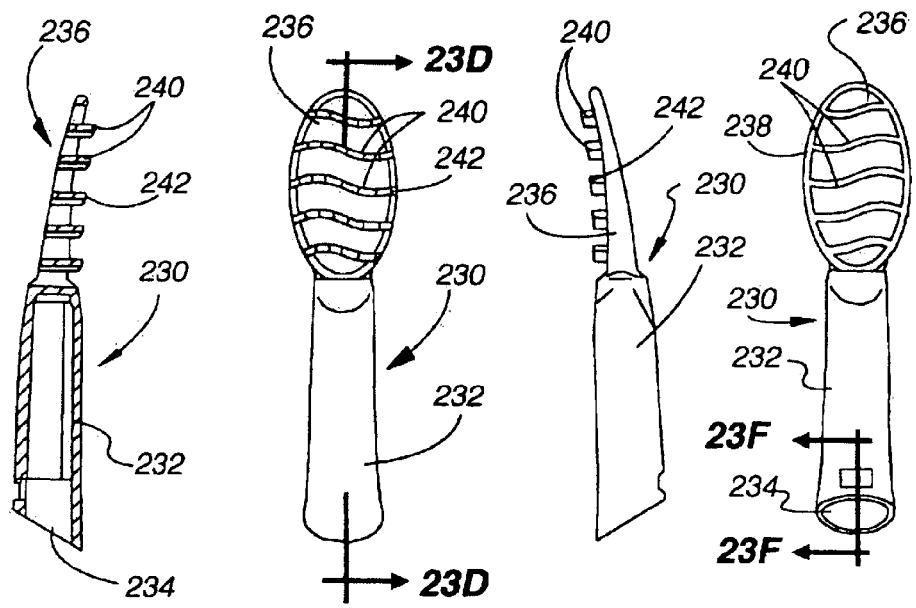
Figures 23F, 23G, 23H:
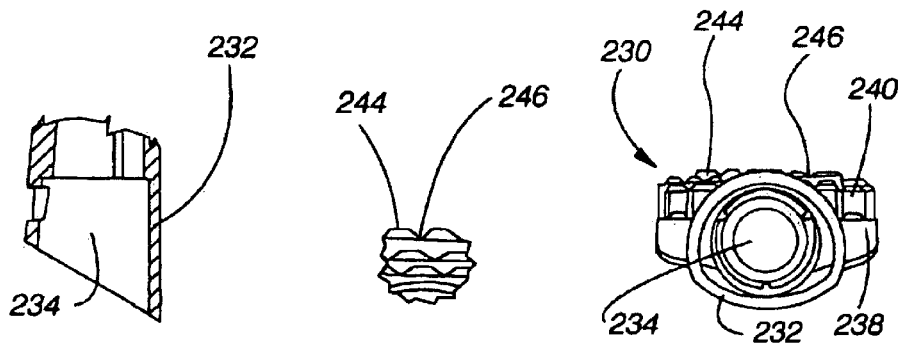

A tongue scraper 230, as shown in FIG. 23A, could also be attached to the shaft 8 so that a user could clean or scrape the tongue. The tongue scraper 230 for attachment to the oral hygiene device 2 of the present invention is shown in further detail in FIGS. 23B–H. This tongue scraper 230 has a sleeve 232 for attachment to the shaft tip 12 extending from the upper handle housing 6. FIGS. 23B and 23F show the attachment structure 234 used to affix this oral hygiene attachment 250 to the upper handle housing 6 of the oral hygiene device 2, which attachment structure 234 is representative of the structures used to attach the other oral hygiene attachments 250 to the oral hygiene device 2. The tongue scraper 230 has a head portion 236 that is formed by an oval frame 238 (as shown from the front in FIG. 23C and from the rear in FIG. 23E) extending with its major axis in line with the length of the sleeve 232. The oval frame 238 curves slightly forward (as shown in the cross section view of FIG. 23B and in the side view of FIG. 23E).

Ribs 240 extend laterally across the head portion 236 within the oval frame 238 (as shown in FIGS. 23C and 23E), and extend forwardly from the oval frame 238 (as shown in FIGS. 23B and 23D). Each rib 240 is curved in a symmetrical manner. The front edge 242 of each lateral rib 240 defines teeth 244 (which may have sloped edges) interspaced by notches 246 (which may be square or V-shaped). The teeth 244 on adjacent ribs 240 are aligned so that none of the notches 246 or teeth 244 are aligned longitudinally along the length of the tongue scraper 230 (as shown in FIGS. 23G and 23H). Thus, no part of the tongue under the tongue scraper 230 is left unscraped when the tongue scraper is pulled along its length (and thus along the tongue).

In one embodiment (best shown in FIG. 7), the tip 12 of the shaft 8 may have one or more slots 18, recesses, indentations, protrusions, or other attachment structures for securely receiving various oral hygiene attachments 250. The tip 12 of the shaft 8 may have an end cap 20, which may further have a dimple or other recess 22, so that an oral hygiene attachment 250 may be attached securely to the tip 12 of the shaft 8 of the oral hygiene device 2. Generally, a detent structure is used to snap-fit the oral hygiene attachment 250 to the tip 12 of the shaft 8. Each oral hygiene attachment 250 fits entirely over and around the shaft 8 and a bottom portion engages the ported nose position 10.

Motors and Basic Circuit

In one embodiment, as shown in FIGS. 4 and 5, the primary motor 30 is a direct current motor operating on an input voltage of approximately 2.4 volts and at this voltage rotates at approximately 14,000 RPM. An eccentric weight 60 is attached to the shaft 58 of the primary motor 30, wherein the eccentric weight 60 is attached to the motor shaft 58 at a location off the center of mass of the eccentric weight 60, thereby creating inertia, which causes the primary motor 30, and thus the structure to which the primary motor 30 is attached, to vibrate. The eccentric weight 60 may be, for example, a brass weight, of SAE standard 72, half hard temper.

The secondary motor 36 is, in one embodiment, capable of rotating at 5,000–9,000 RPM, and operating on approximately 1.4 volts DC. The secondary motor 36 may have an eccentric weight 64 attached to its motor shaft 62 so that as the eccentric weight 64 rotates, the secondary motor 36 vibrates within the shaft 8 of the oral hygiene device 2, thereby imparting a second frequency or set of frequencies of vibration on the shaft 8 of the oral hygiene device 2.

The vibrational frequencies contemplated by the dual motor design range from subsonic frequencies through ultrahigh frequencies depending on the type of motor. For example, an eccentric weight motor may have a frequency of rotation of 300 to 15,000 RPMs while a peizo vibrational motor may have a vibrational frequency of 20,000 hertz or higher. In one embodiment, the ratio of operating frequency between the primary motor 30 and the secondary motor 36 is between approximately 1.3 and 3. This ratio of frequencies has been found to provide the desired level of interference to create pseudo-random, chaotic, motion. The beneficial frequency ratio can vary based on the relative positions of the motors 30, 36 in the oral hygiene device 2, as well as the structural characteristics associated with the attachment of the motors 30, 36 to the oral hygiene device 2.

Figure 34:
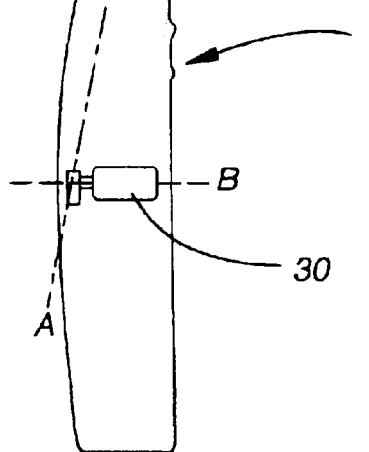
FIGS. 34–39 illustrate the effect of various types of motors on the movement of the head of the oral hygiene device in accordance with one embodiment of the present invention.

As shown in FIGS. 4 and 5, each of the motors 30, 36 are positioned so the motor shafts 58, 62 are aligned along a common or nearly common axis. As shown in FIG. 34, however, the motors 30, 36 may be oriented in the oral hygiene device 2 so the motor shafts 58, 62 extend along axes A and B offset from one another. In FIG. 34, the secondary motor 36 is oriented such that the rotation of the eccentric weight 64 causes an oscillatory, orbital vibrational movement, and the primary motor 30 is mounted such that the axis B of rotation of its motor shaft 58, and corresponding vibration, is at an angle offset from axis A of the secondary motor 36. In FIG. 34, the axis B of rotation of the primary motor 30 is offset approximately 90° from the axis A of rotation of the secondary motor 36. In other embodiments, this offset angle may be less than or greater than 90°. Depending on the frequency and the amplitude of vibration, this combination of motor orientation can create a greater three-dimensional movement of the tip 12, as opposed to the primarily two-dimensional motion of the tip 12 in the embodiment of FIG. 5.

A battery pack 46 may be provided to house two AAA rechargeable batteries 40 in series, thereby providing a power source of 2.4 volts to drive both motors 30, 36. As shown in FIG. 4, a positive lead 34a from the battery pack 46 is coupled with the positive lead 35a of the primary motor 30. The positive lead 35a of the primary motor 30 is coupled through a resistor 39 to the positive lead 41a of the secondary motor 36. The resistor 39 may be sized to reduce the voltage applied to the positive lead 41a of the secondary motor 36 to approximately 1.2 volts. In one embodiment, the resistor 39 may provide a resistivity of 0.62 ohms. In other embodiments, the secondary motor 36 may operate on the same voltage as the primary motor 30 and, therefore, the resistor 39 would be unnecessary. In order to complete the circuit, the negative lead 34b from the battery pack 46 is coupled with a first end of a switch 70, while a second end of the switch 70 is coupled with the negative terminal 35b of the primary motor 30, which is also coupled with the negative terminal 41b of the secondary motor.

In this manner, when the switch 70 is closed by the user pressing the button 14, a voltage of approximately 2.4 volts is applied across the terminals of the primary motor 30, and a voltage of approximately 1.2 volts is applied across the terminals of the secondary motor 36. In the embodiment shown in FIG. 4, the switch 70 utilized may be a single-pole, single-throw switch, which does not change state until it is depressed again by a user. If the switch 70 is closed, when the user again presses the button 14, the switch 70 opens and the circuit shown in FIG. 4 is open, thereby removing power from the motors 30, 36 and turning off the oral hygiene device 2.

In one embodiment, when the user depresses the button 14, power is applied to the primary motor 30 and secondary motor 36 and each begins to rotate its respective eccentric weight 60, 64 about each motor shaft 58, 62. Accordingly, the primary motor 30 moves the shaft 8 of the oral hygiene device 2 relative to the O-ring 24 at approximately the frequency at which the primary motor 36 revolves about the pivot point 25 as limited by the motor mount 50. In this manner, the primary motor 30 imparts a fundamental vibration to the tip 12 of the shaft 8, for example, an orbital motion about a longitudinal axis. In addition, the secondary motor 36 also imparts a vibration to the tip 12 of the shaft 8 at a slower or faster frequency, as desired.

Figure 29:
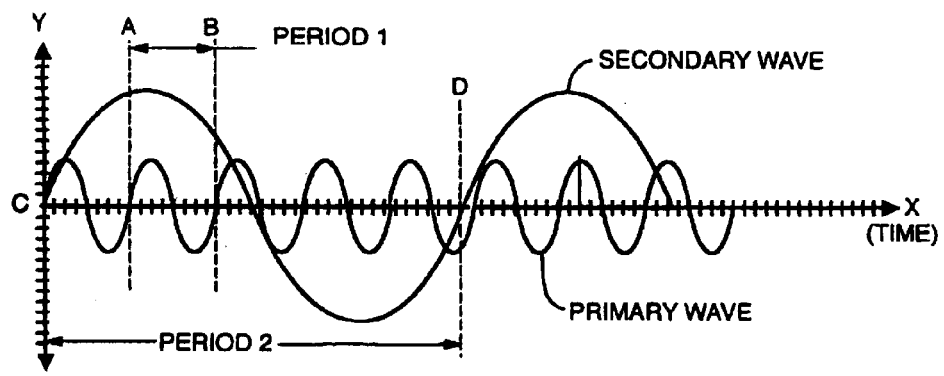
FIG. 29 illustrates the difference in amplitude and frequency of energy imparted by the dual motors in accordance with one embodiment of the present invention.

FIG. 29 shows an exemplary two dimensional representation of vibrational waves created by both the primary motor 30 and the secondary motor 36 in the present invention. One wavelength of the vibration imparted by the primary motor 30 (indicated as "primary wave") starts at point A and ends at point B and one wavelength of the vibration imparted by the secondary motor 36 (indicated as "secondary wave") starts at point C and ends at point D. In FIG. 29, the x-axis represents time and the y-axis distance.

FIGS. 30–33 illustrate the vibrational periods, frequencies, and amplitudes of both motors 30, 36 during operation. The period ("T") of a vibrational wave is the time required for the wave to move a distance equal to one wavelength. As shown FIG. 29, the time it takes a secondary wave to move a distance equal to one secondary wavelength is much greater than the time it takes a primary wave to move a distance equal to one primary wavelength. Therefore, the secondary wave period ("period 2") is much greater than the primary wave period ("period 1").

The frequency ("V") is equal to the number of periods created by a vibration in one second and is equal to 1/T, the inverse of the period. Correspondingly, the primary motor 30 in this embodiment has a higher frequency than the vibrational wave of the secondary motor 36, which has a much longer period.

The amplitude ("A") corresponds to the offset distance between a center axis and the farthest movement of the motor from the center axis. In FIG. 29, the amplitudes of the waves created by the vibration of the motors 30, 36 are shown by the offset of the waveforms from the X-axis in the Y-axis directions. The amplitude of the primary wave created by the primary motor 30 is larger than the amplitude of the secondary wave created by the secondary motor 36. Thus, a gross or large-scale vibrational movement of the tip 12 is caused by the primary motor 30 and the small scale, pseudo-random motion of the tip 12 is caused by the addition of the secondary motor 36.

Figure 30:
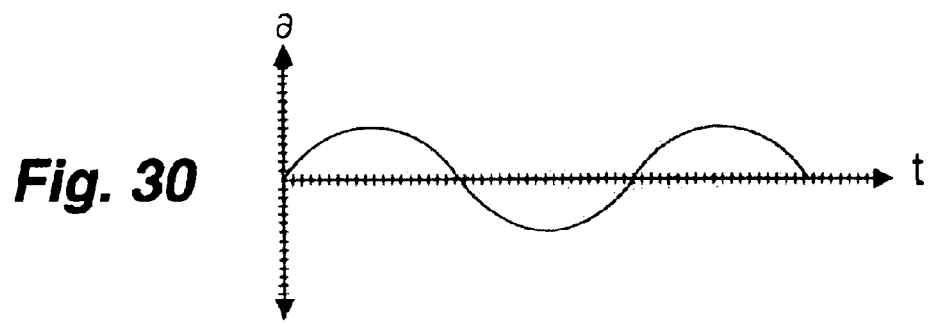
FIG. 30 illustrates the waveform of the energy imparted to the oral hygiene device by a first motor in accordance with one embodiment of the present invention.
Figure 31:
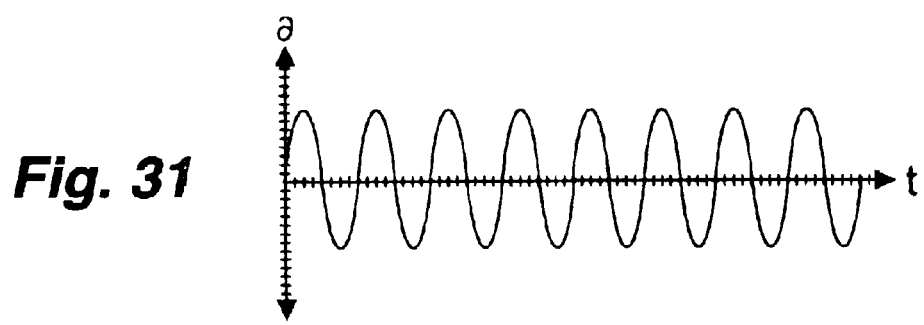
FIG. 31 illustrates the waveform of the energy imparted to the oral hygiene device by a second motor in accordance with one embodiment of the present invention.
Figure 32:
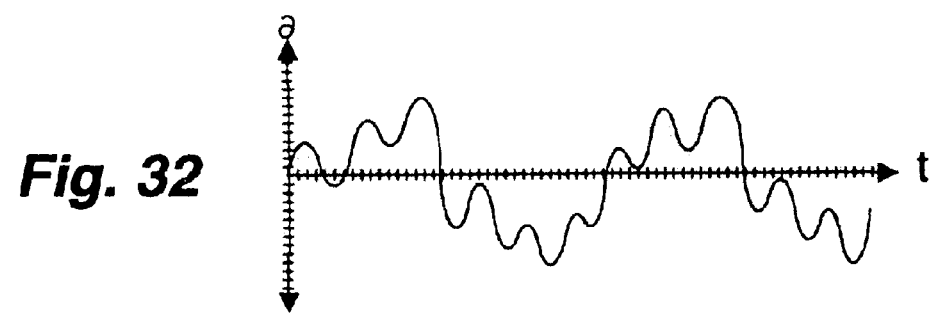
FIG. 32 illustrates the waveform of the effect on the energy imparted to the oral hygiene device by the first motor and the second motor by a mounting structure in accordance with one embodiment of the present invention.
Figure 33:
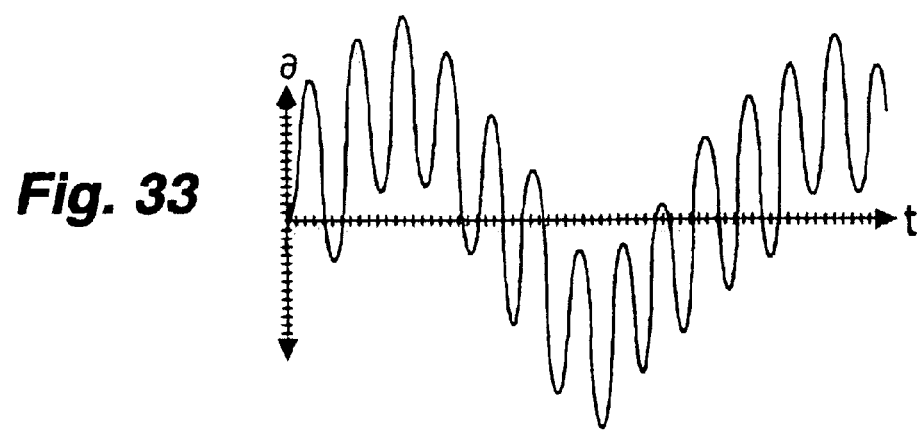
FIG. 33 illustrates sum of the waveforms of FIGS. 30–32 in accordance with one embodiment of the present invention.

Ultimately, the motion of the tip 12 of the oral hygiene device will be the sum of several vibrations and effects including the vibration generated by the primary motor 30, the vibration generated by the secondary motor 36, spring and dampening effects of the O-ring 24, and focusing and dampening effects of the motor mount 50. FIG. 30 represents in two dimensions an isolation of the vibrational motion generated by the secondary motor 36. FIG. 31 represents in two dimensions an isolation of the vibrational motor generated by the primary motor. FIG. 32 represents in two dimensions an isolation of the vibrational motion generated from the O-ring 24 spring effect. FIG. 33 is a representation in two dimensions of a sum of the wave forms in FIGS. 30–32. The end result of the combined motion is a brush head that has a combination of motions. The combination of vibrational motions with varying amplitudes, frequencies, and periods enhances the overall effectiveness of the oral hygiene device 2.

Figure 35:
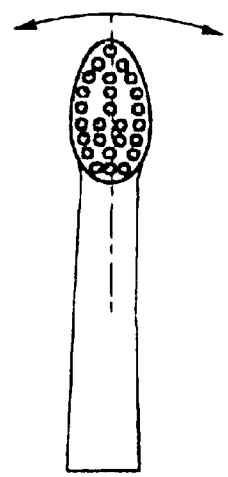
Figure 36:
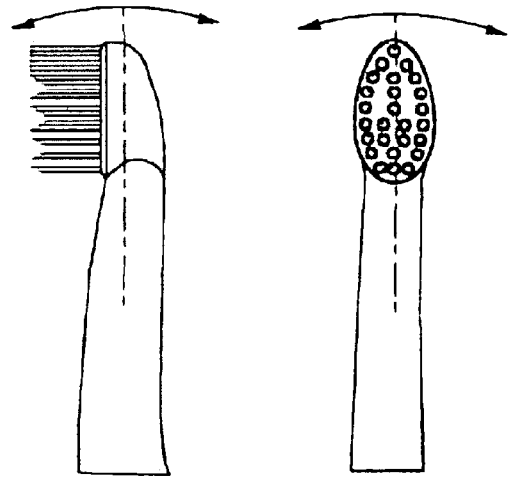

Various movements of the tip 12 created by the primary motor 30 in the oral hygiene device 2 are shown in FIGS. 35–39. In FIG. 35, the tip 12 (shown with a toothbrush 200 attachment) moves in response to a linear vibration, primarily in one dimension from front to back. In FIG. 36, a linear vibratory motion is created primarily in one dimension side-to-side. This second motion may be created by the motor disclosed in U.S. Pat. No. 5,378,153, which is hereby incorporated herein by reference in its entirety.

Figure 37:
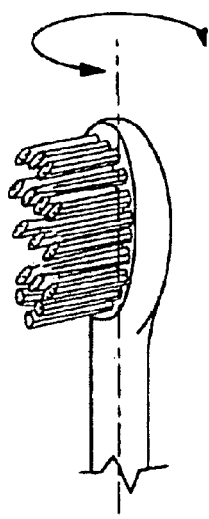

FIG. 37 illustrates an oscillatory, rotational motion of the tip 12 that oscillates about an axis A along the length of the shaft 8 of the oral hygiene device 2. The toothbrush 200 first turns clockwise and then counterclockwise. This type of motion may be created by a motor such as those described in U.S. Pat. Nos. 5,613,259 and 5,341,534, which are hereby incorporated herein by reference in their entirety.

Figure 38:
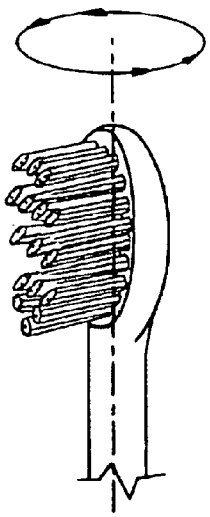

FIG. 38 shows an orbiting motion of the tip 12 about an axis A along the length of the shaft 8 of the oral hygiene device 2. This motion is may be achieved by the use of an eccentric weight motor, for example, a Jinglong Co. (China) model OTL-6CL or equivalent. The orbital motion about the axis A may be continuous in one direction, either clockwise or counterclockwise, if the motor shaft rotates continuously in one direction, or the orbital motion may be oscillatory, first moving clockwise and then counterclockwise along the orbital path, if the motor shaft rotates in an oscillatory pattern.

Figure 39:
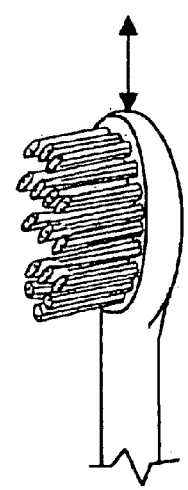

FIG. 39 shows an axial, reciprocating motion along the axis A of the shaft 8. This type of motion can be created by the vibrational motor as disclosed in U.S. Pat. No. 5,226,206, which is hereby incorporated by reference in its entirety.

Figure 18:
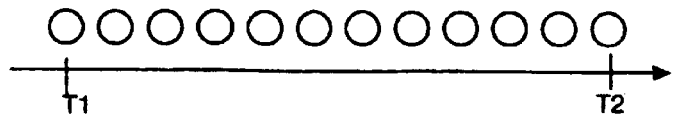
FIG. 18 illustrates front view of a bristle showing an example of bristle motion.
Figure 19:
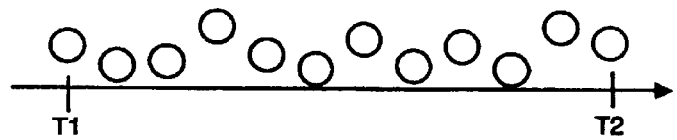
FIG. 19 illustrates front view of a bristle showing an example of bristle motion in accordance with one embodiment of the present invention.

It has been particularly found that the secondary motor 36 imparts a second frequency or set of frequencies of vibration to the shaft 8 during each period of movement of the shaft 8 due to the primary motor 30. This effect is generally illustrated in FIGS. 18 and 19. FIG. 18 shows the motion of a tip of a bristle between time 1 and time 2, where only the primary motor 30 is actuated. The pattern of motion is curvilinear, and is part of the elliptical motion pattern described herein. The bristle tip will return to its position at time 1 as the shaft 8 completes its revolution about the pivot point 25.

FIG. 19 shows the motion of the tip of a bristle during the same time period when both the primary motor 30 and secondary motor 36 are actuated. FIG. 19 shows the divergence of the position of the tip of a bristle, relative to time, from the expected baseline motion created by the primary motor 30 alone. It should be understood that FIGS. 18 and 19 illustrate a single example of a movement of a single bristle tip (or single flosser tip), and the examples of FIGS. 18 and 19 are not intended to limit or characterize all possible bristle movements, either individually or in groups, or the movement of any of the other oral hygiene attachment 250 tips, that may be achieved through the use of various embodiments of the present invention.

FIGS. 18 and 19 do show that the use of two motors can impart different vibrations to the tip 12 of the shaft 8, and thus the tip of the oral hygiene attachment 250, to cause a substantially random movement. Such a random movement allows the oral hygiene device 2 to provide an effective cleaning or polishing effect on a user's teeth. This substantially random movement may not be purely random, but instead may be a complex movement having multiple additive frequency components, creating a pseudo-random state, which may or may not repeat in a periodic or non-periodic manner.

Logic-Based Circuit

Figure 13:
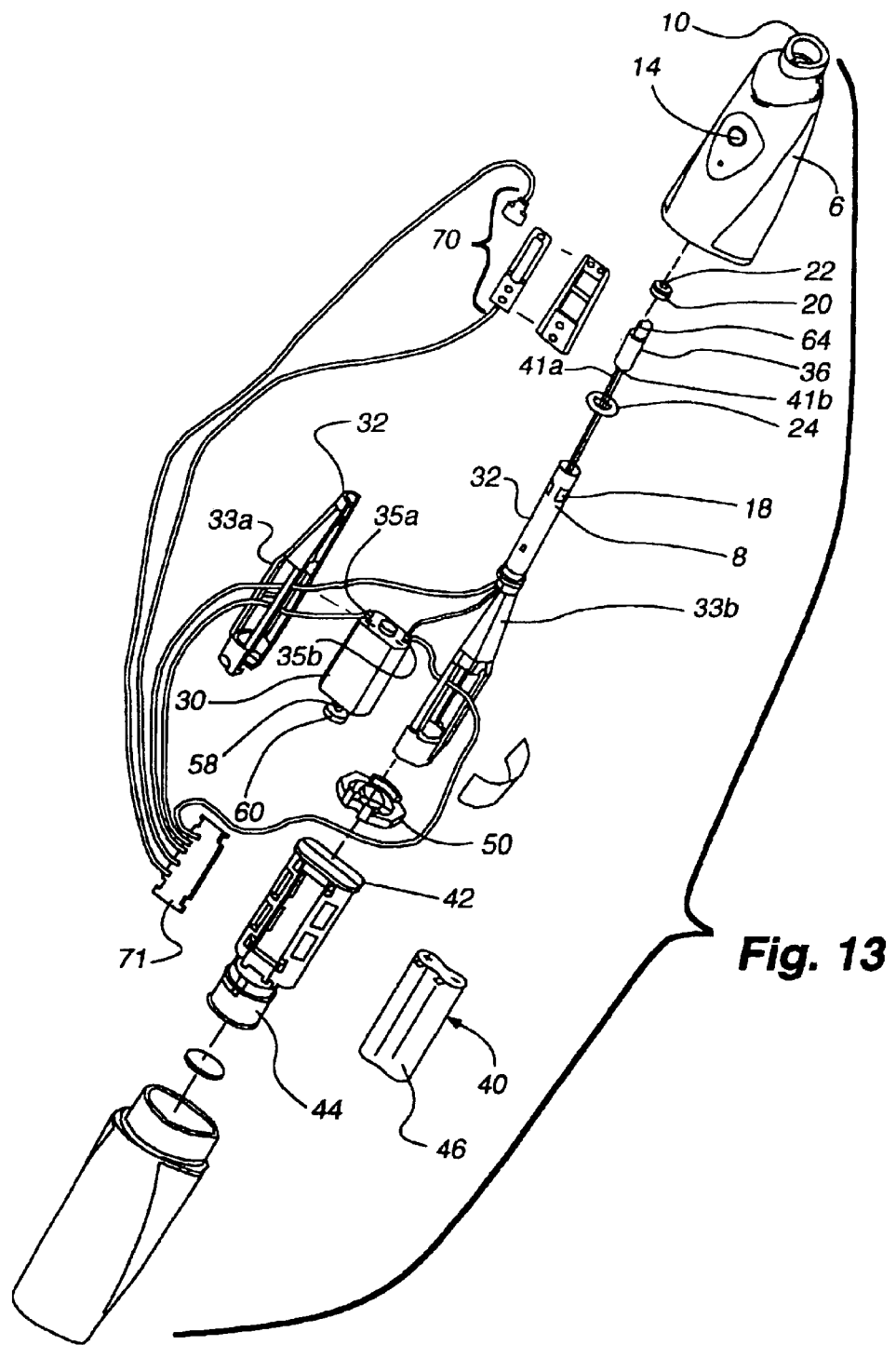
FIG. 13 illustrates an exploded view of an oral hygiene device having a circuit board for controlling the oral hygiene device in accordance with one embodiment of the present invention.
Figure 14A:
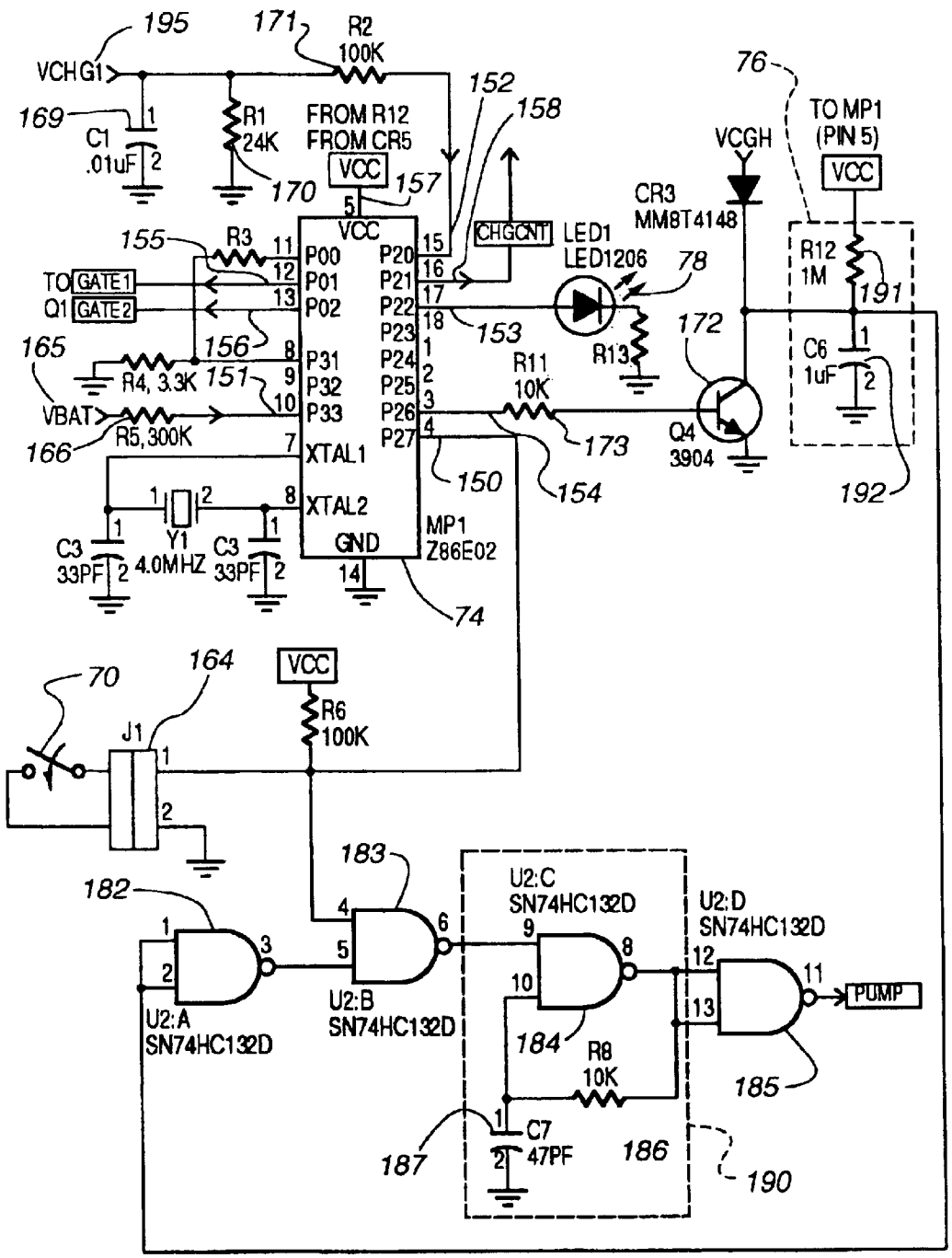
FIGS. 14A–B illustrate a circuit for controlling an oral hygiene device in accordance with one embodiment of the present invention.
Figure 14B:
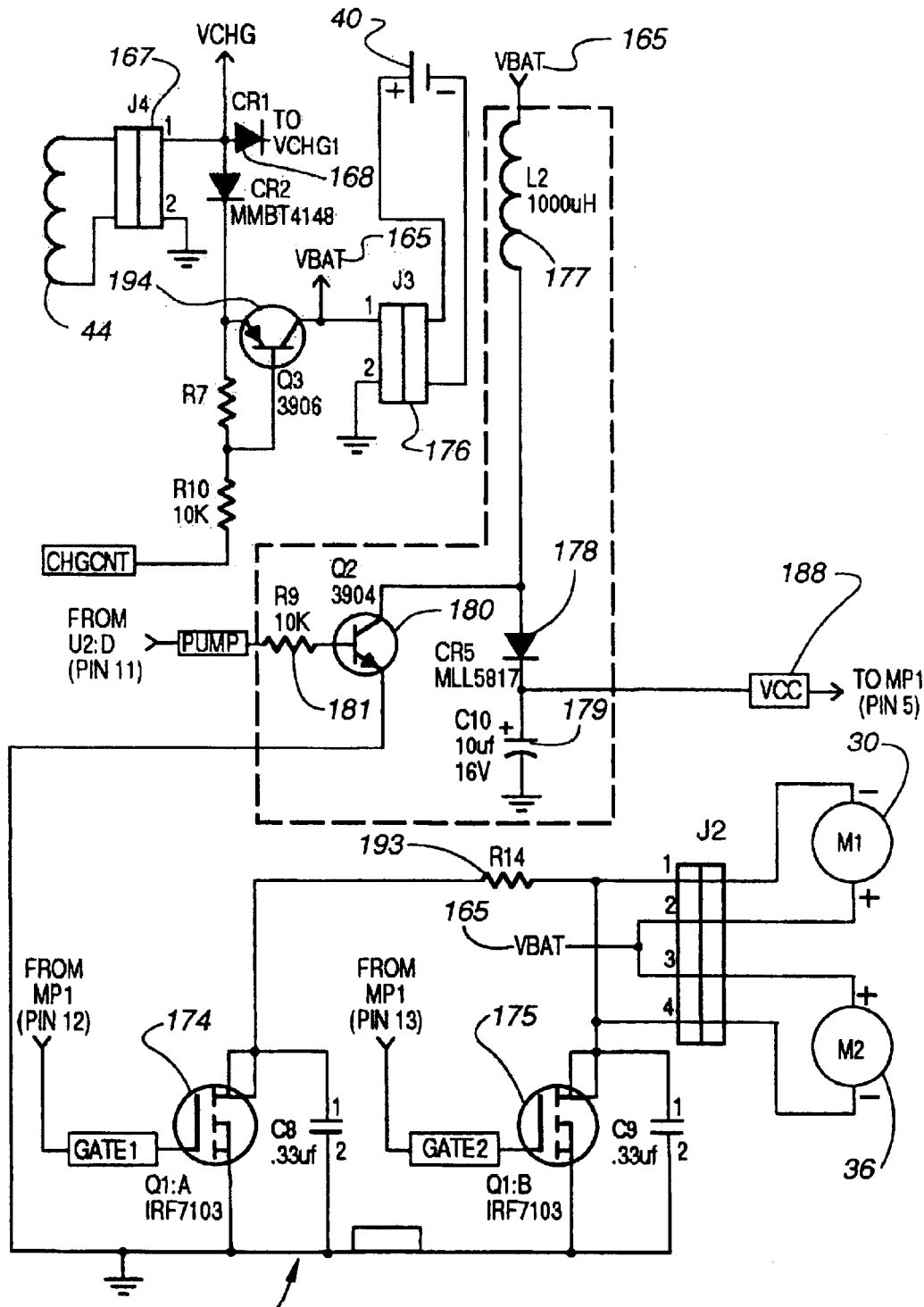

In another embodiment, as shown in FIG. 13, a printed circuit board 71 is attached to the battery bracket 42. The printed circuit board 71 includes a circuit 72 (see FIGS. 14A and 14B) for controlling the operations of the oral hygiene device 2. A microprocessor 74 (see FIGS. 14A and 14B) or other logic device may be provided as part of the circuit 72 to selectively control the operations of the oral hygiene device 2. The microprocessor 74 may be a processor, microcontroller, or other programmable logic device having configurable input/output (I/O) pins operating under the control of a software program stored within the microprocessor 74 or external to the microprocessor 74. FIGS. 14A and 14B illustrate one example of a circuit 72 that may be incorporated into an oral hygiene device 2 of the present invention. In this embodiment, the circuit 72 is provided for controlling the operations of the primary motor 30 and the secondary motor 36 in response to various conditions, for example, user input (depression of the button 14), battery voltage, battery recharging, or other conditions.

Generally, when the user depresses the button 14 to activate the oral hygiene device 2, the microprocessor 74 activates the primary motor 30 to operate at a high speed mode of approximately 13,000–14,000 rpm, for example. The secondary motor 36 is also activated to operate at approximately 9,000 rpm, for example. If, during this "high speed" mode operation, the user depresses the button 14 again, then the microprocessor 74 activates a "low speed" mode wherein the voltage applied to the motors 30, 36 is reduced so that the primary motor 30 and secondary motor 36 rotate at lower speeds, for example, 9,000–10,000 rpm and 6,000 rpm, respectively. If, during the "low speed" mode, the user depresses the button 14 again, then the microprocessor 74 disables both the primary motor 30 and secondary motor 36 and turns off the oral hygiene device 2. While FIG. 14B shows the primary motor 30 and the secondary motor 36 connected in parallel, it is possible to configure the circuit 72 so that each motor 30, 36, and thereby the speed of each motor 30, 36, is separately controlled by the microprocessor 74.

The microprocessor 74 may be further configured to support an automatic shut-off, for example, after 3 minutes of operation. This automatic shut-off function may be implemented by maintaining a timer, which may be programmed within or external to the microprocessor 74. The timer may be initiated upon the detection of the user initially depressing the button 14, and the timer may be stopped either after the user turns off the oral hygiene device 2, or the microprocessor 74 detects that the battery 40 is charging. If the timer expires after the 3 minutes, the microprocessor 74 turns off the motors 30, 36.

If the microprocessor 74 detects that the battery 40 is charging (e.g., after the user has inserted the oral hygiene device 2 into a base charging unit 100 (see FIG. 15)), the microprocessor 74 may illuminate an LED 78 to indicate that charging is occurring. If the oral hygiene device 2 is operating at the time that the oral hygiene device 2 is inserted into the base charging unit 100, the microprocessor 74 may disable both motors 30, 36 so that the oral hygiene device 2 shuts off.

The microprocessor 74 may also support a timer program, which periodically removes power from the motors to provide the user with an indication of the expiration of a time period, for example, a 30 second interval. The microprocessor 74 may, after 30 seconds of operation, disable the power applied to the motors 30, 36 for a short period of time (e.g., 1 to 2 seconds) then reapply power to the motors 30, 36 so that the user is made aware that the oral hygiene device 2 has been operating for 30 seconds. In an alternate embodiment, the power may be interrupted to only the primary motor 30, or to only the secondary motor 36, thus changing the vibratory effect felt by a user, as the indication of the expiration of the time period. In this way, the user can utilize the oral hygiene device 2 on a quadrant of the user's mouth, for example, and then shift the focus of the dental cleaning to another section or quadrant of the user's mouth upon the expiration of the 30 second timer.

The microprocessor 74 may receive a variety of inputs, for example, a switch input 150 (receiving a signal from the switch 70 via connector J1 (164) coupled with input pin 4 (150) of microprocessor 74); a battery level sense input 151 (receiving a signal from the line voltage of the battery 40 at VBAT (165) coupled through a resistor R5 (166) into input pin 10 (151) of the microprocessor 74); and charging coil voltage sense input (152) (receiving a signal from pin 1 of connector J4 (167) through diode CR1 (168) into the circuit of capacitor C1 (169), resistor R1 (170), and resistor R2 (171) coupled with input pin 15 (152) of microprocessor 74) to detect the presence of the charging coil 104 of the base unit 100 (see FIG. 15). In one variation, the switch 70 used in the embodiment of FIG. 14A may be a momentary switch.

The microprocessor 74 outputs may include, for example, an LED output 153 for controlling the illumination of a visual indicator, such as an LED 78 (shown as output pin 17 (153) of the microprocessor 74 driving LED1 (78)); a timer output 154 for controlling a timer circuit 76, which is used to activate a voltage boost circuit (shown as output pin 3 (154) of the microprocessor 74 driving the base of transistor Q4 (172) through resistor R11 (173)); a first motor 30, 36 control output 155 to control the application of a voltage level to the motors 30, 36 (for example, shown as output pin 12 (155) driving the gate of transistor Q1:A (174) to provide a low speed voltage to the motors 30, 36); and a second motor control output 156 to provide a second voltage signal to the motors 30, 36 (shown in this example as output pin 13 (156) of the microprocessor 74 driving the gate of transistor Q1:B (175) in order to provide a voltage for high speed operation of the motors 30, 36).

Referring to FIG. 14B, the terminals of the battery 40 are coupled with the circuit 72 through connector J3 (176), and pin 1 from connector J3 (176) establishes the battery voltage signal VBAT (165) used through the circuit 72. In one embodiment, the batteries 40 used may be nickel metal hydride batteries, which provide a longer life compared to nickel cadmium (Nicad) batteries. Further, nickel metal hydride batteries do not need to be recycled and can be disposed of by the end user. However, a Nicad battery or other rechargeable battery or power source may also be used as another embodiment of the invention. As described above, the batteries 40 may be, for example, two AAA rechargeable batteries connected in series to provide a voltage of approximately 2.4 volts.

One embodiment of the circuit 72 includes a switching power supply, which boosts the voltage of the battery 40 from approximately 2.4 volts to a level of approximately 5 volts, for example. The VBAT (165) signal may be boosted using a boost circuit 189 comprised of inductor L2 (177), diode CR5 (178), capacitor C10 (179), transistor Q2 (180), and resistor R9 (181). An oscillator 190 formed by NAND gate U2:C (184), resistor R8 (186), and capacitor C7 (187) drives the boost section 189 to boost the voltage from the battery 40 to approximately 5 volts as measured between point VCC (188) and ground, as shown in FIG. 14B, by microprocessor 74 at input pin 5 (157), as shown in FIG. 14A.

Accordingly, when the microprocessor 74 sets output pin 3 (154) high, transistor Q4 (172) is actuated and sets the input of NAND gate U2:A (182) low so that input pin 5 of NAND gate U2:B (183) is set high. Assuming the push button 14 is not depressed to actuate switch 70 at this time, then input pin 4 of NAND gate U2:B (183) is also set high, so that the output of NAND gate U2:B (183) is low, which disables the oscillator (190) (formed by NAND gate U2:C (184), resistor R8 (186), and capacitor C7 (187), in this example). Since the oscillator 190 is disabled, the boost section 189 of the circuit 72 is also disabled because the pump signal output of NAND gate U2:D (185) applied to the base of transistor Q2 (180) is low.

In another embodiment of the circuit 72, the microprocessor 74 sets output pin 3 (154) high before entering a sleep mode. In this manner, the microprocessor 74 turns off the oscillator 190 and voltage boost section 189 of the circuit 72 before entering the sleep mode. The RC timer 76 formed by resistor R12 (191) and capacitor C6 (192), however, will begin charging after the microprocessor 74 enters the sleep mode and transistor Q4 (172) turns off. The values of resistor R12 (191) and capacitor C6 (192) may be selected to provide approximately 1 second charging time, whereby after the microprocessor 74 has been asleep for approximately 1 second, the charge on the capacitor C6 (192) is high enough to switch NAND gate U2:A (182) to a low output. When the output of NAND gate U2:A (182) is low, the output of NAND gate U2:B (183) switches high, which actuates the oscillator 190 circuit. When the oscillator 190 is actuated, the voltage boost section 189 is also actuated and the signal VCC (188) increases from approximately 2.4 volts to approximately 5 volts, as described above.

If the microprocessor 74 detects that the supply voltage has been boosted to approximately 5 volts, the microprocessor 74 will wake up from the sleep mode. The microprocessor 74 may then check the state of input pin 4 (150)—which is coupled to the switch 70 through connector J1 (164). If input pin 4 (150) is high, then the push button 14 is not presently depressed or closed by the user to engage the switch 70. The microprocessor 74 may then perform other housekeeping tasks and re-enter sleep mode after turning off the boost section 189 by setting output pin 3 (154) high. This process may repeat periodically (e.g., every 1 second) so the microprocessor 74 can check the state of the switch 70 approximately every 1 second from a sleep state. Also, when the button 14 is pressed closing switch 70, the input pin 4 of NAND gate U2:B (183) is set low and the output of NAND gate U2:B (183) is set high, which actuates the oscillator 190, which further activates the boost circuit 189. This will, in turn, awake the microprocessor 74 from a sleep state.

In another embodiment, when the microprocessor 74 detects a depression of the push button 14 to temporarily close the switch 70, the microprocessor 74 sets the motors 30, 36 to operate in a high speed mode. A high speed mode may be created by setting output pin 13 (156) high, which connects the negative terminals of the motors 30, 36 to ground through the transistor Q1:B (175). In the high speed operation, the battery voltage VBAT (165) (i.e., 2.4 volts) is applied across the terminals of the motors 30, 36. The microprocessor 74 may apply the voltage VBAT (165) across the terminals of the motors 30, 36 for a limited period of time, for example, three minutes.

In a further embodiment, if the microprocessor 74 detects a second depression of the button 14 indicated by a temporary closure of the switch 70 while the motors 30, 36 are driven in a high speed mode, the microprocessor 74 may disable output pin 13 (156) and enable output pin 12 (155). Output pin 12 (155) drives the base of transistor Q1:A (174), which provides a reduced voltage across the terminals of the motors through resistor R14 (193), which may be, for example, 0.68 ohms. In this manner, the motors 30, 36 will then operate in a low speed mode. If, during low speed operations, the microprocessor 74 detects another push button 14 depression indicated by a temporary closure of switch 70, the microprocessor 74 may disable both output pin 12 (155) and output pin 13 (156), thereby disabling both motors 30, 36 from running and deactivating the oral hygiene device 2.

An additional feature may be provided in the circuit of FIGS. 14A and 14B to monitor and charge the battery 40. Microprocessor output pin 16 (158) controls the base of transistor Q3 (194). When the oral hygiene device 2 is placed in a base charging unit 100 (see FIG. 15) transferring voltage through charging coil/magnet 44 and connector J4 (167), the signal VCHG1 (195) from diode CR1 (168) is set high, which is detected by input pin 15 (152) of the microprocessor 74. Further, the microprocessor 74 can track the battery voltage level through input pin 10 (151), which is coupled to the VBAT (165) battery voltage level. Accordingly, when the microprocessor 74 detects that the charging coil/magnet 44 has a voltage from the base charging unit 100, the microprocessor 74 can then determine whether to activate transistor Q3 (193), by setting low the output pin 16 (158) of the microprocessor 74, so that a charging voltage from the charging coil/magnet 44 is applied to the terminals of the rechargeable batteries 40. When output pin 16 (158) is set low, transistor Q3 (193) is activated and the battery 40 charges; when output pin 16

(158) is set high, transistor Q3 (193) is deactivated and the voltage from the charging coil/magnet 44 is no longer applied to the terminals of the battery 40.

In one embodiment, if the microprocessor 74 senses that the battery voltage signal VBAT (165) is too low (e.g., below 2.0 volts) then the microprocessor 74 can disable any motor operations or ignore any depressions of the push button 14 by the user closing the switch 70 until the oral hygiene device 2 has been placed in the base charging unit 100 and the battery voltage is restored to an acceptable level.

In a further embodiment, one or more nickel metal hydride rechargeable batteries 40 may be used in the oral hygiene device 2. In this instance, the microprocessor 74, using one or more persistent timers may keep track, for example, of the amount of time the motors 30, 36 are actuated, the amount of time the battery 40 charges, and the amount of time that the oral hygiene device 2 is both off and not in the base charging unit 100. In this manner, the microprocessor 74 can charge the nickel metal hydride battery 40 using timer information as well as the battery voltage signal VBAT (165) and thereby prevent overcharging of the nickel metal hydride battery 40. If a Nicad or other rechargeable battery 40 is used, the microprocessor 74 may be programmed to charge the battery 40 using, for example, a drip charge method.

While embodiments of the present invention are shown and described in terms of NPN/PNP transistors and field effect transistors, it is understood that other switching devices may be used, for example, n-channel or p-channel CMOS transistors, MOS-FETs, FETs, JFETS, or other similar switching elements or devices. The particular type of switching element used is a matter of choice depending on the particular application of the circuit, and may be based on many factors, for example, power consumption limits, response time, noise immunity, and fabrication considerations.

Further, embodiments of the present invention are described in terms of a circuit which utilizes logic levels of low (e.g., 0 volts) and high (e.g., +5 volts). It is understood that embodiments of the present invention can be utilized in circuits wherein the logic levels are different, for example, in a circuit which utilizes logic levels of 0 volts (logic low) and +3 volts (logic high), or otherwise.

Base Charging Unit

Figure 16:
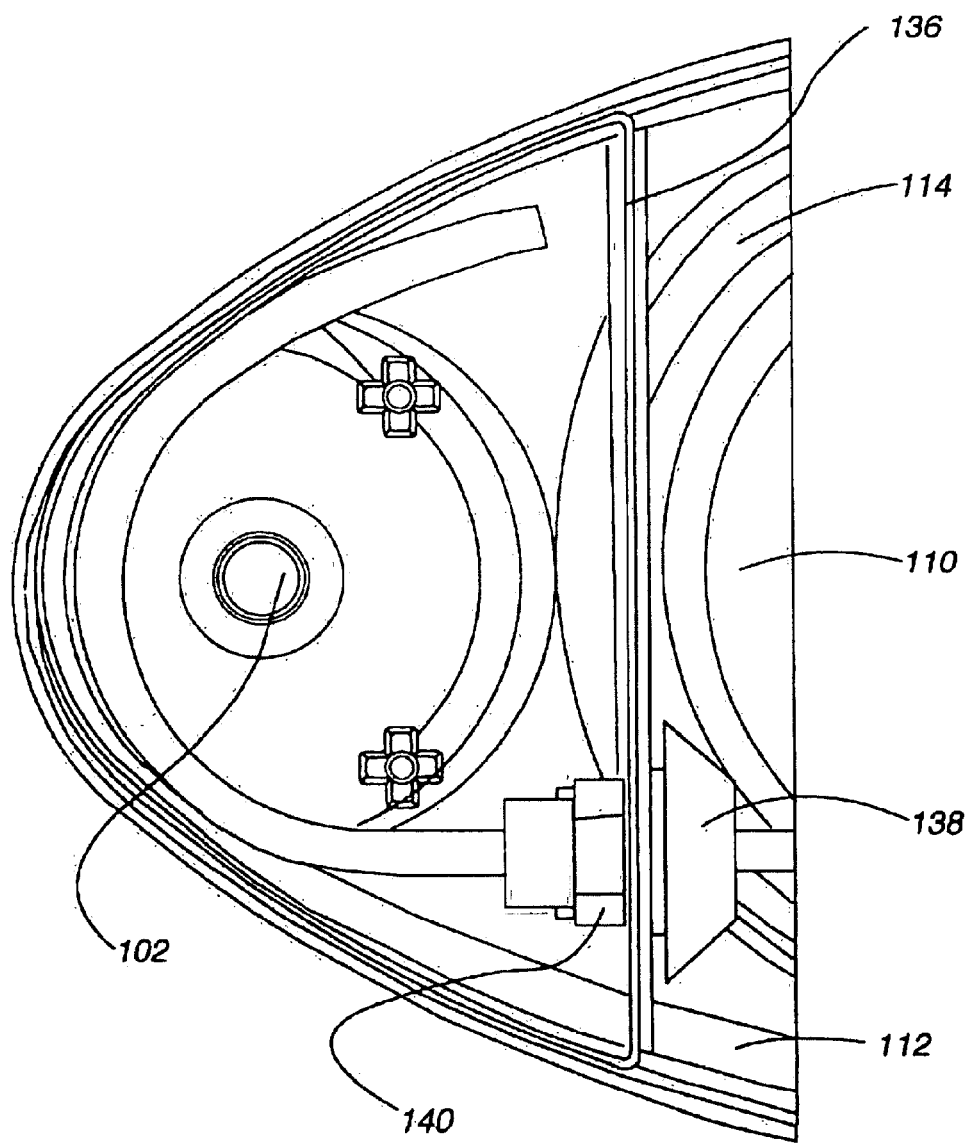
FIG. 16 illustrates a bottom view of a portion of the upper housing portion of the charging base of FIG. 15 in accordance with one embodiment of the present invention.
Figure 17:
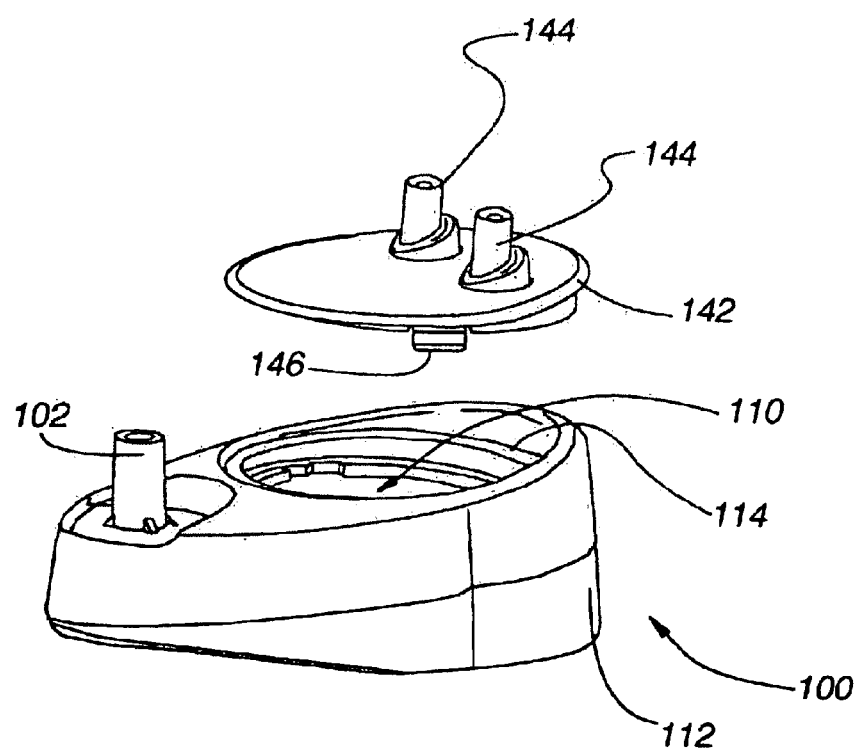
FIG. 17 illustrates an alternative embodiment of a cover for a charging base in accordance with one embodiment of the present invention.

FIGS. 15–17 illustrate a base charging unit 100 for storing the oral hygiene device 2 and the various oral hygiene attachments 250. Further, the base charging unit 100 may include circuitry to provide a charging voltage to the oral hygiene device 2 when the oral hygiene device 2 is placed about the charging post 102 of the base charging unit 100.

As shown in FIG. 15, the base charging unit 100 can be provided with a carousel 106 mounted above a drip cup 108, which is positionable within a cylindrical cavity 110 of the upper housing 112. An annular support ledge 114 of the upper housing 112 supports the drip cup 108 and carousel 106 when positioned in the upper housing 112. The drip cup 108 has a divider 116 with a central recess 118 for accepting a protrusion 120 from the carousel 106 so that the carousel 106 can be removably secured onto the drip cup 108.

A carousel cover 122 fits over the carousel 106 and may be removably secured to the upper housing 112 of the base charging unit 100 by detents 146. The carousel cover 122 may have a small aperture 152 or indention in its top surface to receive a nub 148 on the top of the carousel 106 to aid in the alignment of the carousel 106 with the carousel cover 122. The carousel 106 has a plurality of chambers 124 separated by walls for storing tips or other oral hygiene attachments 250 for the oral hygiene device 2. The drip cup 108 collects any fluids which may drain from the oral hygiene attachments 250 stored in the carousel 106. In one embodiment, each chamber 124 of the carousel 106 has a floor (not shown) upon which rests any oral hygiene attachment 250 stored in the chamber 124. The floor in each chamber 124 has at least one aperture (not shown) for allowing any fluid therein to drain into the drip cup 108. The aperture(s) may be, for example, perforations or conical holes.

The carousel cover 122 has an opening 126 along a portion of its top surface and upper side wall so that a user can deposit oral hygiene attachment 250 tips into or remove them from the carousel 106. Once the drip cup 108, carousel 106, and carousel cover 122 are removably secured within the cylindrical cavity 110 of the upper housing 112, a user can rotate the carousel 106 within the cover 122 by engaging the knurled edge 150 of the carousel 106 exposed in the opening 126 with a finger. The central recess 118 in the drip cup 108 acts as a bearing within which the protrusion 120 of carousel 106 rotates. The user can rotate the carousel 106 until a desired chamber 124 becomes aligned with the opening. The user may insert or remove tips or other oral hygiene attachments 250 for the oral hygiene device 2 into any desired chamber 124, and then rotate the carousel 106 until the filled chamber 124 is covered by the carousel cover, thus protecting the oral hygiene attachments 250.

In one embodiment, the carousel cover 122, the carousel 106, and the drip cup 108 are removable from the upper housing 112 so that a user may remove these elements and wash them, for instance, using a dishwasher. The drip cup 108, carousel 106, and carousel cover 122 may be made of dishwasher safe material, for example, ABS (acrylonitrile butadiene styrene).

The upper housing 112 also has a charging post 102 for engaging a charging post capturing cavity 98 in the bottom end of the oral hygiene device 2 when the user places the oral hygiene device 2 on the charging post 102 for storage or for charging. The charging post 102 contains, in its interior, a cylindrically shaped charging coil 104, which is electrically coupled with a base circuit board assembly 128. The charging coil 104 may be covered with electrical tape 130 if desired. The base circuit board 128 may have circuitry to condition the line voltage received from the AC line power cord 132. In one embodiment, the base circuit board 128 contains circuitry easily adaptable at manufacturing to accommodate different line voltages, for example, 100 volts AC at 50 hertz, 120 volts AC at 60 hertz, 230 volts AC at 50 hertz, or other line voltages. In one embodiment, the charging coil 104 provides a 50,000 hertz AC signal to create an electromagnetic field about the charging coil/magnet 44 of the oral hygiene device 2.

The base circuit board 128 may also have an LED (not shown) on its bottom side in order to illuminate the lower housing 134 of the base charging unit 100 if the lower housing 134 is made of translucent or clear material. In this manner, the LED can provide visual indication that the base charging unit 100 is receiving a line voltage.

As shown in FIG. 16, the upper housing 112 and lower housing 134 have walls 136 defining an area for housing the base circuit board 128. In one embodiment, the wall 136 of the upper housing 112 has an opening to receive the electrical cord 132, which is connected with the base circuit board 128. A grommet 138 may be used to secure the electrical cord 132 within the opening within the wall 136 of the upper housing 112. The grommet 138 may provide a water seal and strain relief for the electrical cord 132. On the opposing side of the wall 136 from the grommet 138, a clip 140 can be used to further secure the electrical cord 132 to the wall 136. The area defined within the interior of the base charging unit 100 between the upper housing 112 and lower housing 134 may be used for storage of the electrical cord 132.

FIG. 17 illustrates an alternative embodiment of the base charging unit 100, wherein a cover 142 has a plurality of posts 144 (two posts are shown in this example). The cover 142 may be adapted to be removably secured within the cylindrical cavity 110 of the upper housing 112. These additional posts 144 can be used to store additional accessories or oral hygiene attachments 250 for the oral hygiene device 2.

All directional references used herein (e.g., front, back, upper, lower, upward, downward, left, right, leftward, rightward, top, bottom, above, below, vertical, horizontal, clockwise, and counterclockwise) are only used for identification purposes to aid the reader's understanding of the present invention, and are not intended to create limitations, particularly as to the position, orientation, or use of the invention.

While the methods disclosed herein have been described and shown with reference to particular operations performed in a particular order, it will be understood that these operations may be combined, sub-divided, or re-ordered to form equivalent methods without departing from the teachings of the present invention. Accordingly, unless specifically indicated herein, the order and grouping of the operations is not a limitation of the present invention.

While the invention has been particularly shown and described with reference to embodiments thereof, it will be understood by those skilled in the art that various other changes in the form and details may be made without departing from the spirit and scope of the invention.

What is claimed is:

1. A power oral hygiene device comprising:
    a main body having a handle portion and a head portion, the head portion comprising at least one of the group consisting of a shaft and an oral hygiene attachment;
    a first vibratory means positioned in the handle portion;
    a second vibratory means positioned in the head portion; and
    a power means for providing energy to the first vibratory means and the second vibratory means.

2. The device of claim 1 further comprising a vibration focusing means attached to the first vibratory means, the vibration focusing means for imparting vibratory energy generated by the first vibratory means to the oral hygiene device in a particular direction.

3. The device of claim 2 further comprising a vibration isolation means for reducing the transfer of vibratory energy, generated by the first vibratory means, from the first vibratory means to the handle portion.

4. The device of claim 3, wherein the vibration focusing means further comprises the vibration isolation means.

5. The device of claim 1 further comprising a vibration isolation means for reducing the transfer of vibratory energy, generated by the second vibratory means, from the second vibratory means to the handle portion.

6. The device of claim 5, wherein the vibration isolation means is positioned between the second vibratory means and the handle portion.

7. The device of claim 1, wherein at least one of the first vibratory means and the second vibratory means comprises an eccentric motor.

8. The device of claim 1, wherein the head portion further comprises a shaft and the second vibratory means is positioned within the shaft.

9. The device of claim 8 further comprising an oral hygiene attachment attached to the shaft.

10. The device of claim 8 further comprising a vibration isolation means for reducing the transfer of vibratory energy, generated by the second vibratory means, from the second vibratory means to the handle portion, wherein the vibration isolation means is positioned between the shaft and the handle portion.

11. The device of claim 1, wherein the head portion further comprises:
    a shaft; and
    an oral hygiene attachment attached to the shaft, wherein the second vibratory means is positioned within the oral hygiene attachment.

12. The device of claim 9 or 11, wherein the oral hygiene attachment comprises at least one attachment selected from a group comprising: a toothbrush head with bristles, an interproximal flossing tip, a tongue scraper, and a prophy polishing cup.

13. The device of claim 1, wherein
    the first vibratory means operates at a first frequency;
    the second vibratory means operates at a second frequency; and
    the first frequency is higher than the second frequency.

14. The device of claim 13, wherein a ratio of the first frequency to the second frequency is between 1.3 and 3.

15. The device of claim 1, wherein the head portion vibrates in a substantially random pattern as a result of a combination of vibratory energy generated by the first vibratory means and vibratory energy generated by the second vibratory means.

16. The device of claim 15 further comprising a frame means for holding the first vibratory means and the second vibratory means, wherein
    the frame means extends between the handle portion and the head portion; and
    the frame means imparts the vibratory energy generated by the first vibratory means to the head portion.

17. The device of claim 1 further comprising a means or changing an operating speed of at least one of the first vibratory means and the second vibratory means from a first speed to a second speed.

18. The device of claim 17, wherein the first speed is higher than the second speed.

19. The device of claim 1 further comprising a vibration isolation means for reducing the transfer of vibratory energy, generated by the first vibratory means, from the first vibratory means to the handle portion.

20. The device of claim 3 or 19, wherein the vibration isolation means is positioned between the first vibratory means and the handle portion.

21. A power oral hygiene device comprising:
    a body having a handle portion and a head portion, the head portion comprising at least one of the group consisting of a shaft and an oral hygiene attachment;
    a first motor operating at a first frequency;
    a second motor operating at a second frequency; and
    a power source for providing energy to operate the first motor and the second motor; wherein the first motor is positioned in the handle portion and the second motor is positioned in the head portion; and a ratio of the first frequency to the second frequency is between 1.3 and 3.

22. The device of claim 21 wherein the head portion further comprises a shaft and the second motor is positioned within the shaft.

23. The device of claim 22 further comprising an oral hygiene attachment attached to the shaft.

24. The device of claim 22 further comprising an elastomeric fitting around the shaft and tightly fitted against an interior surface of the handle portion, wherein the second motor generates vibratory energy and imparts the vibratory energy to the oral hygiene device; and the elastomeric fitting compresses and decompresses in response to the vibratory energy and alters the effect of the vibratory energy of the second motor on the oral hygiene device.

25. The device of claim 24, wherein the elastomeric fitting further reduces the transfer of the vibratory energy generated by the second motor to the handle portion.

26. The device of claim 21, wherein the head portion further comprises:

a shaft; and an oral hygiene attachment attached to the shaft, wherein the second motor is positioned within the oral hygiene attachment.

27. The device of claim 23 or 26, wherein the oral hygiene attachment comprises at least one attachment selected from a group comprising: a toothbrush head with bristles, an interproximal flossing tip, a tongue scraper, and a prophy polishing cup.

28. The device of claim 21 further comprising a motor mount attached to the first motor and tightly fitted against an interior surface of the handle portion, wherein the first motor generates vibratory energy and imparts the vibratory energy to the oral hygiene device; and the motor mount focuses the vibratory energy generated by the first motor and imparts the vibratory energy to the oral hygiene device in at least one direction.

29. The device of claim 28, wherein the motor mount further dampens the vibratory energy generated by the first motor and imparted to the oral hygiene device in at least one direction.

30. The device of claim 28 wherein the motor mount is comprised of an elastomer.

31. The device of claim 28, wherein the motor mount further reduces the transfer of the vibratory energy generated by the first motor to the handle portion.

32. The device of claim 21 further comprising a frame for holding the first motor and the second motor, wherein the frame extends between the handle portion and the head portion; and the frame imparts vibratory energy generated by the first motor to the head portion.

33. The device of claim 21, wherein at least one of the first motor and the second motor comprises an eccentric motor.

34. The device of claim 33, wherein both the first motor and the second motor are eccentric motors, and wherein the first motor and the second motor are positioned such that a first weight on the first motor is oriented in a first direction;

a second weight on the second motor is oriented in a second direction; and the first direction is opposite the second direction.

35. The device of claim 21 further comprising timing system for indicating to a user that the oral hygiene device should be relocated to a different section of the user's mouth.

36. The device of claim 35, the timing system comprises a microprocessor operating under instructions of a timing program.

37. The device of claim 35, wherein the timing system interrupts the operation of at least one of the first motor and the second motor as the indication to the user.

38. The device of claim 21, wherein the head portion vibrates in a substantially random pattern as a result of a combination of vibratory energy generated by the first motor and vibratory energy generated by the second motor.

39. The device of claim 21 further comprising a circuit for changing an operating speed of at least one of the first motor and the second motor from a first speed to a second speed.

40. The device of claim 39, wherein the first speed is higher than the second speed.

41. The device of claim 21, wherein a first motor shaft of the first motor rotates about a first axis and a second motor shaft of the second motor rotates about a second axis.

42. The device of claim 41, wherein the first axis and the second axis comprise a common axis.

43. The device of claim 41, wherein the first axis is offset at an angle from the second axis.

44. The device of claim 41, wherein at least one of the first axis and the second axis is parallel with a longitudinal axis of the head portion.

45. A power toothbrush comprising:

a main body having a handle portion and a head portion, the head portion comprising at least one of the group consisting of a shaft and an oral hygiene attachment;

a first vibratory motor positioned in the handle portion;

a second vibratory motor positioned in the head portion; and a power source for providing energy to the first motor and the second motor.

46. The power toothbrush of claim 45, wherein at least one of the first motor and the second motor is an eccentric motor.

47. The power toothbrush of claim 45, wherein the second vibratory motor is positioned in the brush head portion.

48. The power toothbrush of claim 45, wherein the first vibratory motor operates at a first frequency; and the second motor operates at a second frequency.

49. The power toothbrush of claim 48, wherein a ratio the first frequency to the second frequency is between 1.3 and 3.

* * * * *